(12) United States Patent
Weiss

(10) Patent No.: US 10,392,429 B2
(45) Date of Patent: Aug. 27, 2019

(54) BIPHASIC SINGLE-CHAIN INSULIN ANALOGUES

(71) Applicant: CASE WESTERN RESERVE UNIVERSITY, Cleveland, OH (US)

(72) Inventor: Michael Weiss, Moreland Hills, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 15/517,300

(22) PCT Filed: Oct. 6, 2015

(86) PCT No.: PCT/US2015/054263
§ 371 (c)(1),
(2) Date: Apr. 6, 2017

(87) PCT Pub. No.: WO2016/057529
PCT Pub. Date: Apr. 14, 2016

(65) Prior Publication Data
US 2018/0265560 A1    Sep. 20, 2018

(51) Int. Cl.
*A61K 38/28* (2006.01)
*C07K 14/62* (2006.01)
*A61P 3/10* (2006.01)
*A61K 38/00* (2006.01)
*A61K 9/00* (2006.01)

(52) U.S. Cl.
CPC ............... *C07K 14/62* (2013.01); *A61P 3/10* (2018.01); *A61K 9/0019* (2013.01); *A61K 38/00* (2013.01); *A61K 38/28* (2013.01)

(58) Field of Classification Search
CPC ............................... C07K 14/62; A61K 38/28
See application file for complete search history.

(56) References Cited

U.S. PATENT DOCUMENTS

| | | |
|---|---|---|
| 5,149,716 A | 9/1992 | Vertesy et al. |
| 5,149,777 A | 9/1992 | Hansen et al. |
| 5,422,339 A | 6/1995 | Eisenbarth et al. |
| 5,491,216 A | 2/1996 | Hoffmann et al. |
| 5,506,202 A | 4/1996 | Vertesy et al. |
| 5,618,913 A | 4/1997 | Brange et al. |
| 5,698,669 A | 12/1997 | Hoffmann et al. |
| 5,700,662 A | 12/1997 | Chance et al. |
| 5,716,927 A | 2/1998 | Balschmidt et al. |
| 5,977,297 A | 11/1999 | Obermeier et al. |
| 6,011,007 A | 1/2000 | Havelund et al. |
| 6,221,633 B1 | 4/2001 | Ertl et al. |
| 6,268,335 B1 | 7/2001 | Brader |
| 6,465,426 B2 | 10/2002 | Brader |
| 6,531,448 B1 | 3/2003 | Brader |
| 6,630,348 B1 | 10/2003 | Lee et al. |
| 7,129,211 B2 | 10/2006 | Bhattacharya et al. |
| 7,316,999 B2 | 1/2008 | Hoeg-Jensen et al. |
| 7,547,821 B2 | 6/2009 | Moloney et al. |
| 8,192,857 B2 | 6/2012 | Weiss |
| 2001/0036916 A1 | 11/2001 | Brader |
| 2002/0082199 A1 | 6/2002 | Brader |
| 2003/0104981 A1 | 6/2003 | Mandic |
| 2003/0144181 A1 | 7/2003 | Brader |
| 2004/0014660 A1 | 1/2004 | During et al. |
| 2004/0053816 A1 | 3/2004 | Bhattacharya et al. |
| 2004/0214988 A1 | 10/2004 | Tirrell et al. |
| 2005/0014679 A1 | 1/2005 | Beals et al. |
| 2005/0039235 A1 | 2/2005 | Moloney et al. |
| 2005/0176621 A1 | 8/2005 | Brader et al. |
| 2006/0217290 A1 | 9/2006 | Kohn et al. |
| 2007/0129284 A1 | 6/2007 | Kjeldsen et al. |
| 2008/0146492 A1 | 6/2008 | Zimmerman et al. |
| 2009/0304814 A1 | 12/2009 | Weiss |
| 2010/0099601 A1 | 4/2010 | Weiss |
| 2011/0059887 A1 | 3/2011 | Weiss |

(Continued)

FOREIGN PATENT DOCUMENTS

| | | |
|---|---|---|
| EP | 1 090 640 A2 | 4/2001 |
| WO | 1992/000322 A1 | 9/1992 |

(Continued)

OTHER PUBLICATIONS

PCT/US14/30387 International Search Report and Written Opinion dated Nov. 17, 2014.
Beili Quan, David L. Smiley, Vasily M. Gelfanov and Richard D. DiMarchi, Site Specific Introduction of Unnatural Amino Acids at Sites Critical to Insulin Receptor Recognition and Biological Activity, Understanding Biology Using Peptides, American Peptide Society, 2005, pp. 311-312.
Blanquart et al.; Characterization of IRA/IR hybrid insulin receptors using bioluminescence resonance energy transfer; Biochemical Pharmacology 76 (2008); Jul. 27, 2008, pp. 873-883.
Chen et al.; Sequences of B-Chain/Domain 1-10/1-9 of Insulin and Insulin-like Growth Factor 1 Determine Their Different Folding Behavior; Biochemistry; pp. 9225-9233; 2004.
Currie et al,; The influence of glucose-lowering therapies on cancer risk in type 2 diabetes; Diabetologia; 52(9); pp. 1766-1777; Sep. 2009.

(Continued)

*Primary Examiner* — Gyan Chandra
(74) *Attorney, Agent, or Firm* — Hahn Loeser & Parks LLP; John J. Cunniff

(57) ABSTRACT

A single-chain insulin comprises a C-domain of 6 to 11 amino acid residues comprising at least two acidic residues at the N-terminal side of the C-domain and at least two basic residues at the C-terminal side of the C-domain peptide, a basic amino acid residue at the position corresponding to A8 of human insulin, and an acidic amino acid residue at the position corresponding to A14 of human insulin. The C-domain may contain a 2 to 4 amino acid joint region between the acidic and basic residues. Residues C1 and C2 may have a net negative charge of −1 or −2; and the remaining C-domain segment may culminates with two basic residues. A pharmaceutical composition comprises the single-chain insulin, formulated at a pH within the range 7.0 to 8.0, and may be formulated at a concentration of 0.6 mM to 5.0 mM and/or at a strength of U-100 to U-1000.

20 Claims, 9 Drawing Sheets

Specification includes a Sequence Listing.

(56) References Cited

U.S. PATENT DOCUMENTS

| | | | |
|---|---|---|---|
| 2011/0077196 A1 | 3/2011 | Weiss | |
| 2011/0077197 A1 | 3/2011 | Habermann et al. | |
| 2011/0195896 A1* | 8/2011 | Weiss | A61K 38/28 514/5.9 |
| 2013/0085101 A1 | 4/2013 | Weiss | |
| 2013/0203665 A1 | 8/2013 | DiMarchi et al. | |

FOREIGN PATENT DOCUMENTS

| | | | | |
|---|---|---|---|---|
| WO | 2003/053339 A2 | 7/2003 | | |
| WO | WO-2004085472 A1 * | 10/2004 | | C07K 14/62 |
| WO | 2005/054291 A1 | 6/2005 | | |
| WO | 2007020256 A1 | 2/2007 | | |
| WO | 2007/081824 A2 | 7/2007 | | |
| WO | 2007/096332 A1 | 8/2007 | | |
| WO | 2007/081824 A3 | 2/2008 | | |
| WO | 2008/043033 A2 | 4/2008 | | |
| WO | 2008/043033 A3 | 11/2008 | | |
| WO | 2009/087081 A2 | 7/2009 | | |
| WO | 2009/129250 A2 | 10/2009 | | |
| WO | 2009/132129 A2 | 10/2009 | | |
| WO | 2009133099 A2 | 11/2009 | | |
| WO | 2009/132129 A3 | 1/2010 | | |
| WO | 2009/129250 A3 | 2/2010 | | |
| WO | 2010/014946 A2 | 2/2010 | | |
| WO | 2010014946 A3 | 5/2010 | | |
| WO | 2011028813 A2 | 3/2011 | | |
| WO | 2011072288 A2 | 6/2011 | | |
| WO | 2011103575 A1 | 8/2011 | | |
| WO | 2014071405 A2 | 5/2014 | | |

OTHER PUBLICATIONS

Doig et al.; N- and C-capping preferences for all 20 amino acids n {alpha}-helical peptides; Protein Science; vol. 4; pp. 1325-1335; 1995.

Du et al.; Insulin analogs with B24 or B25 phenylalanine replaced by biphenylalanine; Acta Biochem Biophys Sin; vol. 40, No. 2; pp. 133-139; Feb. 2008.

Duckworth et al, Degradation products of insulin generated by hepatocytes and by insulin protease, Feb. 12, 1988, pp. 1826-1833, vol. 263. No. 4, Journal of Biological Chemistry, US.

EP 07 84 3856 Supplementary European Search Report, 4 pages; dated Dec. 11, 2009.

EP 09 80 3678 Supplemental European Search Report dated Jan. 30, 2012 (dated Jan. 30, 2012).

Garriques et al.; The effect of mutations on the structure of insulin fibrils studied by Fourier transform infrared (FTIR) spectroscopy and electron microscopy; PubMed; vol. 12; 1 page (abstract only); 2002.

Haijuan Du et al. Insulin analogs with B24 or B25 phenylalanine replaced by piphenylalanine, ACTA Biochimica et Biophysica Sinica, Feb. 1, 2008, pp. 133-139, vol. 40, No. 2, Blackwell Publishing, Inc., Malden, MA, US.

Hemkens et al,; Risk of malignancies in patients with diabetes treated with human insulin or insulin analogues: a cohort study; Diabetologia 52(9); pp. 1732-1744; Sep. 2009.

Hua et al.; Mechanism of insulin fibrillation—The structure of insulin under amyloidogenic conditions resembles a protein-folding intermediate, Journal of Biological Chemistry; vol. 279, No. 20; pp. 21449-21460, XP002557730, ISSN 0021-9258; May 14, 2004.

Hua et al.; Design of an Active Ultrastable Single-chain Insulin Analog; The Journal of Biological Chemistry; vol. 283, No. 21; pp. 14703-14716; May 23, 2008.

Huang et al.; Structure-Specific Effects of Protein on Cross β Assembly: Studies of Insulin Fibrillation; Biochemistry 2006, 45, Aug. 4, 2006, pp. 10278-10293.

Kaarsholm et al.; Engineering Stability of the Insulin Monomer Fold with Application to Structure-Activity Relationships; Biochemistry; 32(40); pp. 10773-10778; Oct. 1993.

Kohn et al.; pI-shifted insulin analogs with extended vivo time action and favorable receptor selectivity; Peptides; 28(4); Jan. 25, 2007; pp. 935-948.

Kohn et al.; pI-shifted insulin analogs with extended in vivo time action and favorable receptor selectivity; PubMed; 28(4); 1 page (abstract only); Jan. 25, 2007.

Kristensen et al.; Alanine Scanning Mutagenesis of Insulin; The Journal of Biological Chemistry; vol. 272, No. 20; pp. 12978-12983; May 16, 1997.

Liefvendahl et al.; Mitogenic effect of the insulin analogue glargine in malignant cells in comparison with insulin and IGF-I; PubMed; 1 page (abstract only); Apr. 7, 2008.

Mayer et al.; Proliferative effects of insulin analogues on mammary epithelial cells; Archives of Physiology and Biochemistry; 114(1); pp. 38-44; Feb. 2008.

Milazzo et al.; ASPB10 insulin induction of increased mitogenic responses and phenotypic changes in human breast epithelial cells; evidence for enhanced interactions with the insulin-like growth factor-I receptor; PubMed; 18(1); 1 page (abstract only); Jan. 1997.

Mirmira et al.; Role of the Phenylalanine B24 Side Chain in Directing Insulin Interaction with Its Receptor; The Journal of Biological Chemistry; vol. 264, No. 11; pp. 6349-6354; Apr. 15, 1989.

Mirmira R G et al, Importance of the Character and Configuration of Residues B24 B25 and B26 in Insulin-Receptor Interactions, Jan. 1, 1991, pp. 1428-1436, vol. 266, No. 3, Journal of Biological Chemistry, The American Society of Biological Chemists, Inc., US.

Nakagawa et al,; Chiral Mutagenesis of Insulin; The Journal of Biological Chemistry; vol. 281, No. 31; pp. 22386-22396; Aug. 4, 2006.

Nielsen et al.; Probing the Mechanism of Insulin Fibril Formation with Insulin Mutants; American Chemical Society; Biochemistry; vol. 40; pp. 8397-8409; Jun. 19, 2001.

Olsen et al.; The Relationship Between Insulin Bioactivity and Structure in the NH2-terminal A-chain Helix; Journal of Molecular Biology; vol. 284, Issue 2; pp. 477-488; Nov. 27, 1998.

PCT/US2010/047546 International Search Report and Written Opinion dated May 23, 2011.

PCT/US2010/060085 International Search Report and Written Opinion dated Sep. 16, 2011.

PCT/US2011/25730 International Search Report and Written Opinion dated Jul. 22, 2011.

Raghavendra G. Mirmira et al, Disposition of the Phenylalanine B25 Side Chain during Insulin-Receptor and Insulin-Insulin Interactions, May 1, 1991, pp. 8222-8229, vol. 30, No. 33, Biochemistry, US.

Rajpal et al.; Single-Chain Insulins as Receptor Agonists; The Endocrine Society; 27 pages; Feb. 19, 2009.

Shukla et al,; Analysis of signaling pathways related to cell proliferation stimulated by insulin analogs in human mammary epithelial cell lines; Endocrine-Related Cancer; 16(2); pp. 429-441; Jun. 2009.

Sleiker et al.; Modifications in the B10 and B26-30 regions of the B chain of human insulin alter affinity for the human IGF-I receptor more than for the insulin receptor; Diabetologia; 40 Suppl. 2; 07/0997; pp. S54-S61.

Sreekanth et al.; Structural interpretation of reduced insulin activity as seen in the crystal structure of human Arg-insulin; Biochimie; 90(3); Sep. 22, 2007; pp. 467-473.

Summ et al.; Binding of insulin analogs to partially purified insulin receptor from rat liver membrane (author's trans.); Hoppe Seylers Z. Physiol. Chem.; 357(5); May 1976; pp. 683-693; (Abstract only—1 page).

Teresa Stelmaszynska et al, N-(2-Oxocyl)amino Acids and Nitriles and Final Products of Dipeptide Chlorination Mediated b the Myeloperoxidase/H2O2/CI-System, Dec. 1, 1978, pp. 301-308, vol. 92, No. 1, European Journal of Biochemistry.

Tuffs; German agency suspects that insulin analogue glargine increases risk of cancer; PubMed; BMJ; 339:b2774; 1 page (no abstract available); Jul. 8, 2009.

Wan et al; Enhancing the Activity of Insulin at the Receptor Interface: Crystal Structure and Photo-Cross-Linking of A8 Analogues; Biochemistry 2004, 43; Nov. 25, 2004; pp. 16119-16133.

(56) References Cited

OTHER PUBLICATIONS

Weinstein et al.; Insulin analogues display IGF-I-like mitogenic and anti-apoptotic activities in cultured cancer cells; Diabetes/Metabolism Research and Reviews; 25(1); pp. 41-49; Jan. 2009.

Weiss et al.; Activities of Monomeric Insulin Analogs at Position A8 Are Uncorrelated with Their Thermodynamic Stabilities; The Journal of Biological Chemistry; vol. 276, No. 43; pp. 40018-40024; Oct. 26, 2001.

Weiss et al.; Non-standard Insulin Design: Structure-Activity Relationships at the Periphery of the Insulin Receptor; The Journal of Molecular Biology; vol. 315; pp. 103-111; 2002.

Yang et al. An Achilles' heel in an amyloidogenic protein and its repair: insulin fibrillation and therapeutic design; J Biol Chem. Apr. 2, 2010:285(14): 10806-21.

Zakova et al,; Shortened Insulin Analogues: Marked Changes in Biological Activity Resulting from Replacement of TyrB25 and N-Methylation of Peptide Bonds in the C-Terminus of the B-Chain; Biochemistry; vol. 43; pp. 2323-2331; 2004.

Zelobowska et al.; Mitogenic potency of insulin glargine; Polish Journal of Endocrinology; vol. 60, No. 1; pp. 34-39; 2009.

Zhao et al.; Design of an insulin analog with enhanced receptor binding selectivity: rationale, structure, and therapeutic implications; J. Biol. Chem. 284(46); Sep. 22, 2009; pp. 32178-32187.

Chu, YC et al., The A14 Position of Insulin Tolerates Considerable Structural Alterations with Modest Effects on the Biological Behavior of the Hormone, J. Protein Chem., Oct. 1992, vol. 11, No. 5, pp. 571-577 (abstract only).

Hua, Design of an Active Ultrastable Single-chain Insulin Analog, Journal of Biological Chemistry vol. 283, No. 21, May 23, 2008, pp. 14702-14716, USA.

Hua, Insulin: a small protein with a long journey, Protein & Cell, Higher Education Press and Springer-Verlag Berlin Heidelberg 2010, pp. 537-551.

Huang_The Relationship Between the Connecting Peptide of Recombined Single Chain Insulin and Its Biological Function, Science in China (Series C) vol. 44 No. 6, pp. 593-600, Dec. 2001.

Supplementary European Search Report dated Feb. 7, 2018.

Rajpal, Gautam et al, "Single-Chain Insulins as Receptor Agonists," Molecular Endocrinology, vol. 23, Issue 5, May 2009, pp. 679-688.

Bingham, Emma M. et al, "The Role of Insulin in Human Brain Glucose Metabolism, An Fluoro-Deoxyglucose Positron Emission Tomography Study," Diabetes, vol. 51, Dec. 2002, pp. 3384-3390.

Liu, Hong-Mei et al, "Utilization of Combined Chemical Modifications to Enhance the Blood-Brain Barrier Permeability and Pharmacological Activity of Endomorphin-1," The Journal of Pharmacology and Experimental Therapeutics, vol. 319, No. 1, pp. 308-316.

\* cited by examiner

SEQUENCE LISTING

```
<160> NUMBER OF SEQ ID NOS: 77

<210> SEQ ID NO 1
<211> LENGTH: 86
<212> TYPE: PRT
<213> ORGANISM: Homo sapiens

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 2
<211> LENGTH: 21
<212> TYPE: PRT
<213> ORGANISM: Homo sapiens

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 3
<211> LENGTH: 30
<212> TYPE: PRT
<213> ORGANISM: Homo sapiens

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 4
<211> LENGTH: 30
<212> TYPE: PRT
<213> ORGANISM: Homo sapiens

<400> SEQUENCE: 4

Phe Val Asn Gln His Leu Cys Gly Ser His Leu Val Glu Ala Leu Tyr
1               5                   10                  15
```

```
Leu Val Cys Gly Glu Arg Gly Phe Phe Tyr Thr Lys Pro Thr
            20                  25                  30
```

```
<210> SEQ ID NO 5
<211> LENGTH: 57
<212> TYPE: PRT
<213> ORGANISM: Homo sapiens

<400> SEQUENCE: 5

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn
    50                  55
```

```
<210> SEQ ID NO 6
<211> LENGTH: 57
<212> TYPE: PRT
<213> ORGANISM: Homo sapiens

<400> SEQUENCE: 6

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Glu Gln Leu Glu Asn Tyr Cys Asn
    50                  55
```

```
<210> SEQ ID NO 7
<211> LENGTH: 57
<212> TYPE: PRT
<213> ORGANISM: Homo sapiens

<400> SEQUENCE: 7

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Pro Thr Gly Glu
            20                  25                  30

Gly Pro Arg Arg Gly Ile Val Glu Gln Cys Cys His Ser Ile Cys Ser
        35                  40                  45

Leu Glu Gln Leu Glu Asn Tyr Cys Asn
    50                  55
```

```
<210> SEQ ID NO 8
<211> LENGTH: 57
<212> TYPE: PRT
<213> ORGANISM: Homo sapiens

<400> SEQUENCE: 8

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Pro Thr Glu Glu
            20                  25                  30

Gly Pro Arg Arg Gly Ile Val Glu Gln Cys Cys His Ser Ile Cys Ser
        35                  40                  45
```

Leu Glu Gln Leu Glu Asn Tyr Cys Asn
            50                  55

<210> SEQ ID NO 9
<211> LENGTH: 57
<212> TYPE: PRT
<213> ORGANISM: Homo sapiens

<400> SEQUENCE: 9

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Pro Thr Glu Glu
            20                  25                  30

Gly Pro Arg Arg Gly Ile Val Glu Gln Cys Cys His Ser Ile Cys Ser
        35                  40                  45

Trp Glu Gln Leu Glu Asn Tyr Cys Asn
            50                  55

<210> SEQ ID NO 10
<211> LENGTH: 57
<212> TYPE: PRT
<213> ORGANISM: Homo sapiens

<400> SEQUENCE: 10

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Glu Thr Glu Glu
            20                  25                  30

Gly Pro Arg Arg Gly Ile Val Glu Gln Cys Cys His Ser Ile Cys Ser
        35                  40                  45

Leu Glu Gln Leu Glu Asn Tyr Cys Asn
            50                  55

<210> SEQ ID NO 11
<211> LENGTH: 57
<212> TYPE: PRT
<213> ORGANISM: Homo sapiens

<400> SEQUENCE: 11

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Arg Thr Glu Glu
            20                  25                  30

Gly Pro Arg Arg Gly Ile Val Glu Gln Cys Cys His Ser Ile Cys Ser
        35                  40                  45

Leu Glu Gln Leu Glu Asn Tyr Cys Asn
            50                  55

<210> SEQ ID NO 12
<211> LENGTH: 57
<212> TYPE: PRT
<213> ORGANISM: Homo sapiens

<400> SEQUENCE: 12

Phe Val Asn Gln His Leu Cys Gly Ser His Leu Val Glu Ala Leu Tyr
1               5                   10                  15

Leu Val Cys Gly Glu Arg Gly Phe Phe Tyr Thr Glu Pro Thr Glu Glu
            20                  25                  30

Gly Pro Arg Arg Gly Ile Val Glu Gln Cys Cys His Ser Ile Cys Ser

```
                    35                  40                  45

Leu Glu Gln Leu Glu Asn Tyr Cys Asn
        50                  55

<210> SEQ ID NO 13
<211> LENGTH: 54
<212> TYPE: PRT
<213> ORGANISM: Homo sapiens

<400> SEQUENCE: 13

Gln His Leu Cys Gly Ser His Leu Val Glu Ala Leu Tyr Leu Val Cys
1               5                   10                  15

Gly Glu Arg Gly Phe Phe Tyr Thr Pro Glu Thr Glu Glu Gly Pro Arg
            20                  25                  30

Arg Gly Ile Val Glu Gln Cys Cys His Ser Ile Cys Ser Leu Glu Gln
        35                  40                  45

Leu Glu Asn Tyr Cys Asn
    50

<210> SEQ ID NO 14
<211> LENGTH: 57
<212> TYPE: PRT
<213> ORGANISM: Homo sapiens

<400> SEQUENCE: 14

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Pro Thr Glu Glu
            20                  25                  30

Gly Pro Arg Arg Gly Ile Val Glu Gln Cys Cys His Ser Ile Cys Ser
        35                  40                  45

Leu Glu Gln Leu Glu Asn Tyr Cys Asn
    50                  55

<210> SEQ ID NO 15
<211> LENGTH: 56
<212> TYPE: PRT
<213> ORGANISM: Homo sapiens

<400> SEQUENCE: 15

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Pro Thr Glu Glu
            20                  25                  30

Gly Arg Arg Gly Ile Val Glu Gln Cys Cys His Ser Ile Cys Ser Leu
        35                  40                  45

Glu Gln Leu Glu Asn Tyr Cys Asn
    50                  55

<210> SEQ ID NO 16
<211> LENGTH: 55
<212> TYPE: PRT
<213> ORGANISM: Homo sapiens

<400> SEQUENCE: 16

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Pro Thr Glu Glu
            20                  25                  30
```

Arg Arg Gly Ile Val Glu Gln Cys Cys His Ser Ile Cys Ser Leu Glu
            35                  40                  45

Gln Leu Glu Asn Tyr Cys Asn
    50                  55

<210> SEQ ID NO 17
<211> LENGTH: 54
<212> TYPE: PRT
<213> ORGANISM: Homo sapiens

<400> SEQUENCE: 17

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Pro Thr Glu Glu
            20                  25                  30

Arg Gly Ile Val Glu Gln Cys Cys His Ser Ile Cys Ser Leu Glu Gln
            35                  40                  45

Leu Glu Asn Tyr Cys Asn
    50

<210> SEQ ID NO 18
<211> LENGTH: 57
<212> TYPE: PRT
<213> ORGANISM: Homo sapiens

<400> SEQUENCE: 18

Phe Val Asn Gln His Leu Cys Gly Ser His Leu Val Gln Ala Leu Tyr
1               5                   10                  15

Leu Val Cys Gly Glu Arg Gly Phe Phe Tyr Thr Pro Thr Glu Thr Glu Glu
            20                  25                  30

Gly Pro Arg Arg Gly Ile Val Glu Gln Cys Cys His Ser Ile Cys Ser
            35                  40                  45

Leu Glu Gln Leu Glu Asn Tyr Cys Asn
    50                  55

<210> SEQ ID NO 19
<211> LENGTH: 54
<212> TYPE: PRT
<213> ORGANISM: Homo sapiens

<400> SEQUENCE: 19

Gln His Leu Cys Gly Ser His Leu Val Glu Ala Leu Tyr Leu Val Cys
1               5                   10                  15

Gly Glu Arg Gly Phe Phe Tyr Thr Asp Pro Thr Glu Glu Gly Pro Arg
            20                  25                  30

Arg Gly Ile Val Glu Gln Cys Cys His Ser Ile Cys Ser Leu Glu Gln
            35                  40                  45

Leu Glu Asn Tyr Cys Asn
    50

<210> SEQ ID NO 20
<211> LENGTH: 56
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (43)..(43)

```
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (49)..(49)
<223> OTHER INFORMATION: Xaa is chosen from the group Gln, Glu, Phe,
      Trp, or Tyr

<400> SEQUENCE: 20

Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Pro Thr Glu Ser
            20                  25                  30

Pro Arg Arg Gly Ile Val Glu Gln Cys Cys Xaa Ser Ile Cys Ser Leu
        35                  40                  45

Xaa Gln Leu Glu Asn Tyr Cys Asn
    50                  55

<210> SEQ ID NO 21
<211> LENGTH: 57
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (44)..(44)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (50)..(50)
<223> OTHER INFORMATION: Xaa is chosen from the group Gln, Glu, Phe,
      Trp, or Tyr

<400> SEQUENCE: 21

Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Pro Thr Ser Glu
            20                  25                  30

Gly Pro Arg Arg Gly Ile Val Glu Gln Cys Cys Xaa Ser Ile Cys Ser
        35                  40                  45

Leu Xaa Gln Leu Glu Asn Tyr Cys Asn
    50                  55

<210> SEQ ID NO 22
<211> LENGTH: 57
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (44)..(44)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (50)..(50)
<223> OTHER INFORMATION: Xaa is chosen from the group Gln, Glu, Phe,
      Trp, or Tyr

<400> SEQUENCE: 22
```

-continued

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Pro Thr Gly Glu
            20                  25                  30

Gly Pro Arg Arg Gly Ile Val Glu Gln Cys Cys Xaa Ser Ile Cys Ser
        35                  40                  45

Leu Xaa Gln Leu Glu Asn Tyr Cys Asn
    50                  55
```

<210> SEQ ID NO 23
<211> LENGTH: 57
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (44)..(44)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (50)..(50)
<223> OTHER INFORMATION: Xaa is chosen from the group Gln, Glu, Phe,
      Trp, or Tyr

<400> SEQUENCE: 23

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Pro Thr Glu Glu
            20                  25                  30

Gly Pro Arg Arg Gly Ile Val Glu Gln Cys Cys Xaa Ser Ile Cys Ser
        35                  40                  45

Leu Xaa Gln Leu Glu Asn Tyr Cys Asn
    50                  55
```

<210> SEQ ID NO 24
<211> LENGTH: 57
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (44)..(44)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (49)..(49)
<223> OTHER INFORMATION: Xaa is chosen from the group Ala, Arg, Glu,
      Lys, or Pro
<220> FEATURE:
<221> NAME/KEY: MISC_FEATURE
<222> LOCATION: (50)..(50)
<223> OTHER INFORMATION: Xaa is chosen from the group Gln, Glu, Phe,
      Trp, or Tyr

<400> SEQUENCE: 24

```
Phe Val Asn Gln His Leu Cys Gly Ser His Leu Val Glu Ala Leu Tyr
1               5                   10                  15
```

```
Leu Val Cys Gly Glu Arg Gly Phe Phe Tyr Thr Xaa Pro Thr Glu Glu
         20                  25                  30

Gly Pro Arg Arg Gly Ile Val Glu Gln Cys Cys Xaa Ser Ile Cys Ser
         35                  40                  45

Xaa Xaa Gln Leu Glu Asn Tyr Cys Asn
         50                  55

<210> SEQ ID NO 25
<211> LENGTH: 57
<212> TYPE: PRT
<213> ORGANISM: Homo sapiens
<220> FEATURE:
<221> NAME/KEY: MISC_FEATURE
<222> LOCATION: (29)..(29)
<223> OTHER INFORMATION: Xaa is chosen from the group Ala, Arg, Glu,
      Lys, or Pro
<220> FEATURE:
<221> NAME/KEY: MISC_FEATURE
<222> LOCATION: (44)..(44)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (50)..(50)
<223> OTHER INFORMATION: Xaa is chosen from the group Gln, Glu, Phe,
      Trp, or Tyr

<400> SEQUENCE: 25

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Xaa Thr Glu Glu
         20                  25                  30

Gly Pro Arg Arg Gly Ile Val Glu Gln Cys Cys Xaa Ser Ile Cys Ser
         35                  40                  45

Leu Xaa Gln Leu Glu Asn Tyr Cys Asn
         50                  55

<210> SEQ ID NO 26
<211> LENGTH: 57
<212> TYPE: PRT
<213> ORGANISM: Homo sapiens
<220> FEATURE:
<221> NAME/KEY: MISC_FEATURE
<222> LOCATION: (29)..(29)
<223> OTHER INFORMATION: Xaa is chosen from the group Ala, Arg, Glu,
      Lys, or Pro
<220> FEATURE:
<221> NAME/KEY: MISC_FEATURE
<222> LOCATION: (44)..(44)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (50)..(50)
<223> OTHER INFORMATION: Xaa is chosen from the group Gln, Glu, Phe,
      Trp, or Tyr

<400> SEQUENCE: 26

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Xaa Thr Glu Glu
         20                  25                  30

Gly Pro Arg Arg Gly Ile Val Glu Gln Cys Cys Xaa Ser Ile Cys Ser
         35                  40                  45

Leu Xaa Gln Leu Glu Asn Tyr Cys Asn
         50                  55
```

```
<210> SEQ ID NO 27
<211> LENGTH: 57
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Glu,
      Lys, or Pro
<220> FEATURE:
<221> NAME/KEY: MISC_FEATURE
<222> LOCATION: (44)..(44)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (50)..(50)
<223> OTHER INFORMATION: Xaa is chosen from the group Gln, Glu, Phe,
      Trp, or Tyr

<400> SEQUENCE: 27

Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Pro Thr Glu Glu
            20                  25                  30

Gly Pro Arg Arg Gly Ile Val Glu Gln Cys Cys Xaa Ser Ile Cys Ser
        35                  40                  45

Leu Xaa Gln Leu Glu Asn Tyr Cys Asn
    50                  55

<210> SEQ ID NO 28
<211> LENGTH: 54
<212> TYPE: PRT
<213> ORGANISM: Homo sapiens
<220> FEATURE:
<221> NAME/KEY: MISC_FEATURE
<222> LOCATION: (26)..(26)
<223> OTHER INFORMATION: Xaa is chosen from the group Ala, Arg, Glu,
      Lys, or Pro
<220> FEATURE:
<221> NAME/KEY: MISC_FEATURE
<222> LOCATION: (41)..(41)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (47)..(47)
<223> OTHER INFORMATION: Xaa is chosen from the group Gln, Glu, Phe,
      Trp, or Tyr

<400> SEQUENCE: 28

Gln His Leu Cys Gly Ser His Leu Val Glu Ala Leu Tyr Leu Val Cys
1               5                   10                  15

Gly Glu Arg Gly Phe Phe Tyr Thr Pro Xaa Thr Glu Glu Gly Pro Arg
            20                  25                  30

Arg Gly Ile Val Glu Gln Cys Cys Xaa Ser Ile Cys Ser Leu Xaa Gln
        35                  40                  45

Leu Glu Asn Tyr Cys Asn
    50

<210> SEQ ID NO 29
<211> LENGTH: 57
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
```

```
     Asp, Gln, Glu, or Lys
<220> FEATURE:
<221> NAME/KEY: MISC_FEATURE
<222> LOCATION: (44)..(44)
<223> OTHER INFORMATION: Xaa is chosen from the group Ala, Arg, Gln,
     Glu, or Lys
<220> FEATURE:
<221> NAME/KEY: MISC_FEATURE
<222> LOCATION: (50)..(50)
<223> OTHER INFORMATION: Xaa is chosen from the group Gln, Glu, Phe,
     Trp, or Tyr

<400> SEQUENCE: 29

Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Pro Thr Glu Glu
            20                  25                  30

Gly Pro Arg Arg Gly Ile Val Glu Gln Cys Cys Xaa Ser Ile Cys Ser
        35                  40                  45

Leu Xaa Gln Leu Glu Asn Tyr Cys Asn
    50                  55

<210> SEQ ID NO 30
<211> LENGTH: 56
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
     Asp, Gln, Glu, or Lys
<220> FEATURE:
<221> NAME/KEY: MISC_FEATURE
<222> LOCATION: (43)..(43)
<223> OTHER INFORMATION: Xaa is chosen from the group Ala, Arg, Gln,
     Glu, or Lys
<220> FEATURE:
<221> NAME/KEY: MISC_FEATURE
<222> LOCATION: (49)..(49)
<223> OTHER INFORMATION: Xaa is chosen from the group Gln, Glu, Phe,
     Trp, or Tyr

<400> SEQUENCE: 30

Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Pro Thr Glu Glu
            20                  25                  30

Gly Arg Arg Gly Ile Val Glu Gln Cys Cys Xaa Ser Ile Cys Ser Leu
        35                  40                  45

Xaa Gln Leu Glu Asn Tyr Cys Asn
    50                  55

<210> SEQ ID NO 31
<211> LENGTH: 55
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
     Asp, Gln, Glu, or Lys
<220> FEATURE:
<221> NAME/KEY: MISC_FEATURE
<222> LOCATION: (42)..(42)
<223> OTHER INFORMATION: Xaa is chosen from the group Ala, Arg, Gln,
     Glu, or Lys
<220> FEATURE:
<221> NAME/KEY: MISC_FEATURE
<222> LOCATION: (48)..(48)
```

<223> OTHER INFORMATION: Xaa is chosen from the group Gln, Glu, Phe,
      Trp, or Tyr

<400> SEQUENCE: 31

Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Pro Thr Glu Glu
            20                  25                  30

Arg Arg Gly Ile Val Glu Gln Cys Cys Xaa Ser Ile Cys Ser Leu Xaa
        35                  40                  45

Gln Leu Glu Asn Tyr Cys Asn
    50                  55

<210> SEQ ID NO 32
<211> LENGTH: 54
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (41)..(41)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (47)..(47)
<223> OTHER INFORMATION: Xaa is chosen from the group Gln, Glu, Phe,
      Trp, or Tyr

<400> SEQUENCE: 32

Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Pro Thr Glu Glu
            20                  25                  30

Arg Gly Ile Val Glu Gln Cys Cys Xaa Ser Ile Cys Ser Leu Xaa Gln
        35                  40                  45

Leu Glu Asn Tyr Cys Asn
    50

<210> SEQ ID NO 33
<211> LENGTH: 57
<212> TYPE: PRT
<213> ORGANISM: Homo sapiens
<220> FEATURE:
<221> NAME/KEY: MISC_FEATURE
<222> LOCATION: (29)..(29)
<223> OTHER INFORMATION: Xaa is chosen from the group Ala, Arg, Glu,
      Lys, or Pro
<220> FEATURE:
<221> NAME/KEY: MISC_FEATURE
<222> LOCATION: (44)..(44)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (50)..(50)
<223> OTHER INFORMATION: Xaa is chosen from the group Gln, Glu, Phe,
      Trp, or Tyr

<400> SEQUENCE: 33

Phe Val Asn Gln His Leu Cys Gly Ser His Leu Val Gln Ala Leu Tyr
1               5                   10                  15

Leu Val Cys Gly Glu Arg Gly Phe Phe Tyr Thr Pro Xaa Thr Glu Glu

```
                   20                  25                  30

Gly Pro Arg Arg Gly Ile Val Glu Gln Cys Cys Xaa Ser Ile Cys Ser
             35                  40                  45

Leu Xaa Gln Leu Glu Asn Tyr Cys Asn
     50                  55

<210> SEQ ID NO 34
<211> LENGTH: 54
<212> TYPE: PRT
<213> ORGANISM: Homo sapiens
<220> FEATURE:
<221> NAME/KEY: MISC_FEATURE
<222> LOCATION: (25)..(25)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (41)..(41)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (47)..(47)
<223> OTHER INFORMATION: Xaa is chosen from the group Gln, Glu, Phe,
      Trp, or Tyr

<400> SEQUENCE: 34

Gln His Leu Cys Gly Ser His Leu Val Glu Ala Leu Tyr Leu Val Cys
1               5                  10                  15

Gly Glu Arg Gly Phe Phe Tyr Thr Xaa Pro Thr Glu Glu Gly Pro Arg
                20                  25                  30

Arg Gly Ile Val Glu Gln Cys Cys Xaa Ser Ile Cys Ser Leu Xaa Gln
             35                  40                  45

Leu Glu Asn Tyr Cys Asn
     50

<210> SEQ ID NO 35
<211> LENGTH: 57
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (31)..(31)
<223> OTHER INFORMATION: Xaa is either Asp or Glu
<220> FEATURE:
<221> NAME/KEY: MISC_FEATURE
<222> LOCATION: (44)..(44)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (50)..(50)
<223> OTHER INFORMATION: Xaa is chosen from the group Gln, Glu, Phe,
      Trp, or Tyr

<400> SEQUENCE: 35

Phe Val Asn Gln His Leu Cys Gly Ser His Leu Val Glu Ala Leu Tyr
1               5                  10                  15

Leu Val Cys Gly Glu Arg Gly Phe Phe Tyr Thr Xaa Pro Thr Xaa Ser
                20                  25                  30

Gly Pro Arg Arg Gly Ile Val Glu Gln Cys Cys Xaa Ser Ile Cys Ser
             35                  40                  45
```

```
Leu Xaa Gln Leu Glu Asn Tyr Cys Asn
    50                  55
```

<210> SEQ ID NO 36
<211> LENGTH: 57
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
    Asp, Gln, Glu, or Lys
<220> FEATURE:
<221> NAME/KEY: MISC_FEATURE
<222> LOCATION: (32)..(32)
<223> OTHER INFORMATION: Xaa is either Asp or Glu
<220> FEATURE:
<221> NAME/KEY: MISC_FEATURE
<222> LOCATION: (44)..(44)
<223> OTHER INFORMATION: Xaa is chosen from the group Ala, Arg, Gln,
    Glu, or Lys
<220> FEATURE:
<221> NAME/KEY: MISC_FEATURE
<222> LOCATION: (50)..(50)
<223> OTHER INFORMATION: Xaa is chosen from the group Gln, Glu, Phe,
    Trp, or Tyr

<400> SEQUENCE: 36

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Pro Thr Ser Xaa
                20                  25                  30

Gly Pro Arg Arg Gly Ile Val Glu Gln Cys Cys Xaa Ser Ile Cys Ser
            35                  40                  45

Leu Xaa Gln Leu Glu Asn Tyr Cys Asn
    50                  55
```

<210> SEQ ID NO 37
<211> LENGTH: 57
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
    Asp, Gln, Glu, or Lys
<220> FEATURE:
<221> NAME/KEY: MISC_FEATURE
<222> LOCATION: (31)..(31)
<223> OTHER INFORMATION: Xaa is either Asp or Glu
<220> FEATURE:
<221> NAME/KEY: MISC_FEATURE
<222> LOCATION: (44)..(44)
<223> OTHER INFORMATION: Xaa is chosen from the group Ala, Arg, Gln,
    Glu, or Lys
<220> FEATURE:
<221> NAME/KEY: MISC_FEATURE
<222> LOCATION: (50)..(50)
<223> OTHER INFORMATION: Xaa is chosen from the group Gln, Glu, Phe,
    Trp, or Tyr

<400> SEQUENCE: 37

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Pro Thr Xaa Glu
                20                  25                  30

Gly Pro Arg Arg Gly Ile Val Glu Gln Cys Cys Xaa Ser Ile Cys Ser
            35                  40                  45

Leu Xaa Gln Leu Glu Asn Tyr Cys Asn
```

-continued

```
        50                  55

<210> SEQ ID NO 38
<211> LENGTH: 57
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (31)..(32)
<223> OTHER INFORMATION: Xaa are each either Asp or Glu
<220> FEATURE:
<221> NAME/KEY: MISC_FEATURE
<222> LOCATION: (44)..(44)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (50)..(50)
<223> OTHER INFORMATION: Xaa is chosen from the group Gln, Glu, Phe,
      Trp, or Tyr

<400> SEQUENCE: 38

Phe Val Asn Gln His Leu Cys Gly Ser His Leu Val Glu Ala Leu Tyr
1               5                  10                  15

Leu Val Cys Gly Glu Arg Gly Phe Phe Tyr Thr Xaa Pro Thr Xaa Xaa
            20                  25                  30

Gly Pro Arg Arg Gly Ile Val Glu Gln Cys Cys Xaa Ser Ile Cys Ser
        35                  40                  45

Leu Xaa Gln Leu Glu Asn Tyr Cys Asn
    50                  55

<210> SEQ ID NO 39
<211> LENGTH: 57
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (31)..(32)
<223> OTHER INFORMATION: Xaa are each either Asp or Glu
<220> FEATURE:
<221> NAME/KEY: MISC_FEATURE
<222> LOCATION: (44)..(44)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (49)..(49)
<223> OTHER INFORMATION: Xaa is chosen from the group Ala, Arg, Glu,
      Lys, or Pro
<220> FEATURE:
<221> NAME/KEY: MISC_FEATURE
<222> LOCATION: (50)..(50)
<223> OTHER INFORMATION: Xaa is chosen from the group Gln, Glu, Phe,
      Trp, or Tyr

<400> SEQUENCE: 39

Phe Val Asn Gln His Leu Cys Gly Ser His Leu Val Glu Ala Leu Tyr
1               5                  10                  15

Leu Val Cys Gly Glu Arg Gly Phe Phe Tyr Thr Xaa Pro Thr Xaa Xaa
            20                  25                  30
```

Gly Pro Arg Arg Gly Ile Val Glu Gln Cys Cys Xaa Ser Ile Cys Ser
        35                  40                  45

Xaa Xaa Gln Leu Glu Asn Tyr Cys Asn
    50                  55

<210> SEQ ID NO 40
<211> LENGTH: 57
<212> TYPE: PRT
<213> ORGANISM: Homo sapiens
<220> FEATURE:
<221> NAME/KEY: MISC_FEATURE
<222> LOCATION: (29)..(29)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (31)..(32)
<223> OTHER INFORMATION: Xaa are each either Asp or Glu
<220> FEATURE:
<221> NAME/KEY: MISC_FEATURE
<222> LOCATION: (44)..(44)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (50)..(50)
<223> OTHER INFORMATION: Xaa is chosen from the group Gln, Glu, Phe,
      Trp, or Tyr

<400> SEQUENCE: 40

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Xaa Thr Xaa Xaa
            20                  25                  30

Gly Pro Arg Arg Gly Ile Val Glu Gln Cys Cys Xaa Ser Ile Cys Ser
        35                  40                  45

Leu Xaa Gln Leu Glu Asn Tyr Cys Asn
    50                  55

<210> SEQ ID NO 41
<211> LENGTH: 57
<212> TYPE: PRT
<213> ORGANISM: Homo sapiens
<220> FEATURE:
<221> NAME/KEY: MISC_FEATURE
<222> LOCATION: (29)..(29)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (31)..(32)
<223> OTHER INFORMATION: Xaa are each either Asp or Glu
<220> FEATURE:
<221> NAME/KEY: MISC_FEATURE
<222> LOCATION: (44)..(44)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (50)..(50)
<223> OTHER INFORMATION: Xaa is chosen from the group Gln, Glu, Phe,
      Trp, or Tyr

<400> SEQUENCE: 41

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Xaa Thr Xaa Xaa
            20                  25                  30

Gly Pro Arg Arg Gly Ile Val Glu Gln Cys Cys Xaa Ser Ile Cys Ser

```
                35                  40                  45

Leu Xaa Gln Leu Glu Asn Tyr Cys Asn
    50                  55

<210> SEQ ID NO 42
<211> LENGTH: 57
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (31)..(32)
<223> OTHER INFORMATION: Xaa are each either Asp or Glu
<220> FEATURE:
<221> NAME/KEY: MISC_FEATURE
<222> LOCATION: (44)..(44)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (50)..(50)
<223> OTHER INFORMATION: Xaa is chosen from the group Gln, Glu, Phe,
      Trp, or Tyr

<400> SEQUENCE: 42

Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Pro Thr Xaa Xaa
            20                  25                  30

Gly Pro Arg Arg Gly Ile Val Glu Gln Cys Cys Xaa Ser Ile Cys Ser
        35                  40                  45

Leu Xaa Gln Leu Glu Asn Tyr Cys Asn
    50                  55

<210> SEQ ID NO 43
<211> LENGTH: 54
<212> TYPE: PRT
<213> ORGANISM: Homo sapiens
<220> FEATURE:
<221> NAME/KEY: MISC_FEATURE
<222> LOCATION: (26)..(26)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (28)..(29)
<223> OTHER INFORMATION: Xaa are each either Asp or Glu
<220> FEATURE:
<221> NAME/KEY: MISC_FEATURE
<222> LOCATION: (41)..(41)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (47)..(47)
<223> OTHER INFORMATION: Xaa is chosen from the group Gln, Glu, Phe,
      Trp, or Tyr

<400> SEQUENCE: 43

Gln His Leu Cys Gly Ser His Leu Val Glu Ala Leu Tyr Leu Val Cys
1               5                   10                  15

Gly Glu Arg Gly Phe Phe Tyr Thr Pro Xaa Thr Xaa Xaa Gly Pro Arg
            20                  25                  30

Arg Gly Ile Val Glu Gln Cys Cys Xaa Ser Ile Cys Ser Leu Xaa Gln
        35                  40                  45
```

```
Leu Glu Asn Tyr Cys Asn
    50
```

<210> SEQ ID NO 44
<211> LENGTH: 57
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (31)..(32)
<223> OTHER INFORMATION: Xaa are each either Asp or Glu
<220> FEATURE:
<221> NAME/KEY: MISC_FEATURE
<222> LOCATION: (44)..(44)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (50)..(50)
<223> OTHER INFORMATION: Xaa is chosen from the group Gln, Glu, Phe,
      Trp, or Tyr

<400> SEQUENCE: 44

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Pro Thr Xaa Xaa
            20                  25                  30

Gly Pro Arg Arg Gly Ile Val Glu Gln Cys Cys Xaa Ser Ile Cys Ser
        35                  40                  45

Leu Xaa Gln Leu Glu Asn Tyr Cys Asn
    50                  55
```

<210> SEQ ID NO 45
<211> LENGTH: 56
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (31)..(32)
<223> OTHER INFORMATION: Xaa are each either Asp or Glu
<220> FEATURE:
<221> NAME/KEY: MISC_FEATURE
<222> LOCATION: (43)..(43)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (49)..(49)
<223> OTHER INFORMATION: Xaa is chosen from the group Gln, Glu, Phe,
      Trp, or Tyr

<400> SEQUENCE: 45

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Pro Thr Xaa Xaa
            20                  25                  30

Gly Arg Arg Gly Ile Val Glu Gln Cys Cys Xaa Ser Ile Cys Ser Leu
        35                  40                  45
```

Xaa Gln Leu Glu Asn Tyr Cys Asn
    50                  55

<210> SEQ ID NO 46
<211> LENGTH: 55
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (31)..(32)
<223> OTHER INFORMATION: Xaa are each either Asp or Glu
<220> FEATURE:
<221> NAME/KEY: MISC_FEATURE
<222> LOCATION: (42)..(42)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (48)..(48)
<223> OTHER INFORMATION: Xaa is chosen from the group Gln, Glu, Phe,
      Trp, or Tyr

<400> SEQUENCE: 46

Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Pro Thr Xaa Xaa
            20                  25                  30

Arg Arg Gly Ile Val Glu Gln Cys Cys Xaa Ser Ile Cys Ser Leu Xaa
        35                  40                  45

Gln Leu Glu Asn Tyr Cys Asn
    50                  55

<210> SEQ ID NO 47
<211> LENGTH: 54
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (31)..(32)
<223> OTHER INFORMATION: Xaa are each either Asp or Glu
<220> FEATURE:
<221> NAME/KEY: MISC_FEATURE
<222> LOCATION: (41)..(41)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (47)..(47)
<223> OTHER INFORMATION: Xaa is chosen from the group Gln, Glu, Phe,
      Trp, or Tyr

<400> SEQUENCE: 47

Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Pro Thr Xaa Xaa
            20                  25                  30

Arg Gly Ile Val Glu Gln Cys Cys Xaa Ser Ile Cys Ser Leu Xaa Gln
        35                  40                  45

Leu Glu Asn Tyr Cys Asn

```
<210> SEQ ID NO 48
<211> LENGTH: 57
<212> TYPE: PRT
<213> ORGANISM: Homo sapiens
<220> FEATURE:
<221> NAME/KEY: MISC_FEATURE
<222> LOCATION: (29)..(29)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (31)..(32)
<223> OTHER INFORMATION: Xaa are each either Asp or Glu
<220> FEATURE:
<221> NAME/KEY: MISC_FEATURE
<222> LOCATION: (44)..(44)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (50)..(50)
<223> OTHER INFORMATION: Xaa is chosen from the group Gln, Glu, Phe,
      Trp, or Tyr

<400> SEQUENCE: 48

Phe Val Asn Gln His Leu Cys Gly Ser His Leu Val Gln Ala Leu Tyr
1               5                   10                  15

Leu Val Cys Gly Glu Arg Gly Phe Phe Tyr Thr Pro Xaa Thr Xaa Xaa
            20                  25                  30

Gly Pro Arg Arg Gly Ile Val Glu Gln Cys Cys Xaa Ser Ile Cys Ser
        35                  40                  45

Leu Xaa Gln Leu Glu Asn Tyr Cys Asn
    50                  55

<210> SEQ ID NO 49
<211> LENGTH: 54
<212> TYPE: PRT
<213> ORGANISM: Homo sapiens
<220> FEATURE:
<221> NAME/KEY: MISC_FEATURE
<222> LOCATION: (25)..(25)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (28)..(29)
<223> OTHER INFORMATION: Xaa are each either Asp or Glu
<220> FEATURE:
<221> NAME/KEY: MISC_FEATURE
<222> LOCATION: (41)..(41)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (47)..(47)
<223> OTHER INFORMATION: Xaa is chosen from the group Gln, Glu, Phe,
      Trp, or Tyr

<400> SEQUENCE: 49

Gln His Leu Cys Gly Ser His Leu Val Glu Ala Leu Tyr Leu Val Cys
1               5                   10                  15

Gly Glu Arg Gly Phe Phe Tyr Thr Xaa Pro Thr Xaa Xaa Gly Pro Arg
            20                  25                  30

Arg Gly Ile Val Glu Gln Cys Cys Xaa Ser Ile Cys Ser Leu Xaa Gln
        35                  40                  45

Leu Glu Asn Tyr Cys Asn
    50
```

```
<210> SEQ ID NO 50
<211> LENGTH: 62
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (31)..(31)
<223> OTHER INFORMATION: Xaa is either Asp or Glu
<220> FEATURE:
<221> NAME/KEY: MISC_FEATURE
<222> LOCATION: (35)..(39)
<223> OTHER INFORMATION: Xaa are each optionally present and may be
      drawn from the group Ala, Asn, Gln, Gly, Pro, Ser or Thr
<220> FEATURE:
<221> NAME/KEY: MISC_FEATURE
<222> LOCATION: (49)..(49)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (55)..(55)
<223> OTHER INFORMATION: Xaa is chosen from the group Gln, Glu, Phe,
      Trp, or Tyr

<400> SEQUENCE: 50

Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Pro Thr Xaa Ser
            20                  25                  30

Gly Pro Xaa Xaa Xaa Xaa Xaa Arg Arg Gly Ile Val Glu Gln Cys Cys
        35                  40                  45

Xaa Ser Ile Cys Ser Leu Xaa Gln Leu Glu Asn Tyr Cys Asn
    50                  55                  60

<210> SEQ ID NO 51
<211> LENGTH: 62
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (32)..(32)
<223> OTHER INFORMATION: Xaa is either Asp or Glu
<220> FEATURE:
<221> NAME/KEY: MISC_FEATURE
<222> LOCATION: (35)..(39)
<223> OTHER INFORMATION: Xaa are each optionally present and may be
      drawn from the group Ala, Asn, Gln, Gly, Pro, Ser or Thr
<220> FEATURE:
<221> NAME/KEY: MISC_FEATURE
<222> LOCATION: (49)..(49)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (55)..(55)
<223> OTHER INFORMATION: Xaa is chosen from the group Gln, Glu, Phe,
      Trp, or Tyr

<400> SEQUENCE: 51

Phe Val Asn Gln His Leu Cys Gly Ser His Leu Val Glu Ala Leu Tyr
1               5                   10                  15
```

```
Leu Val Cys Gly Glu Arg Gly Phe Phe Tyr Thr Xaa Pro Thr Ser Xaa
            20                  25                  30

Gly Pro Xaa Xaa Xaa Xaa Xaa Arg Arg Gly Ile Val Glu Gln Cys Cys
            35                  40                  45

Xaa Ser Ile Cys Ser Leu Xaa Gln Leu Glu Asn Tyr Cys Asn
 50                  55                  60

<210> SEQ ID NO 52
<211> LENGTH: 62
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (31)..(31)
<223> OTHER INFORMATION: Xaa is either Asp or Glu
<220> FEATURE:
<221> NAME/KEY: MISC_FEATURE
<222> LOCATION: (35)..(39)
<223> OTHER INFORMATION: Xaa are each optionally present and may be
      drawn from the group Ala, Asn, Gln, Gly, Pro, Ser or Thr
<220> FEATURE:
<221> NAME/KEY: MISC_FEATURE
<222> LOCATION: (49)..(49)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (55)..(55)
<223> OTHER INFORMATION: Xaa is chosen from the group Gln, Glu, Phe,
      Trp, or Tyr

<400> SEQUENCE: 52

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Xaa Pro Thr Xaa Glu
            20                  25                  30

Gly Pro Xaa Xaa Xaa Xaa Xaa Arg Arg Gly Ile Val Glu Gln Cys Cys
            35                  40                  45

Xaa Ser Ile Cys Ser Leu Xaa Gln Leu Glu Asn Tyr Cys Asn
 50                  55                  60

<210> SEQ ID NO 53
<211> LENGTH: 62
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (31)..(32)
<223> OTHER INFORMATION: Xaa are each either Asp or Glu
<220> FEATURE:
<221> NAME/KEY: MISC_FEATURE
<222> LOCATION: (35)..(39)
<223> OTHER INFORMATION: Xaa are each optionally present and may be
      drawn from the group Ala, Asn, Gln, Gly, Pro, Ser or Thr
<220> FEATURE:
<221> NAME/KEY: MISC_FEATURE
<222> LOCATION: (49)..(49)
<223> OTHER INFORMATION: Xaa is chosen from the group Ala, Arg, Gln,
      Glu, or Lys
<220> FEATURE:
```

<221> NAME/KEY: MISC_FEATURE
<222> LOCATION: (55)..(55)
<223> OTHER INFORMATION: Xaa is chosen from the group Gln, Glu, Phe,
    Trp, or Tyr

<400> SEQUENCE: 53

Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Pro Thr Xaa Xaa
            20                  25                  30

Gly Pro Xaa Xaa Xaa Xaa Xaa Arg Arg Gly Ile Val Glu Gln Cys Cys
        35                  40                  45

Xaa Ser Ile Cys Ser Leu Xaa Gln Leu Glu Asn Tyr Cys Asn
50                  55                  60

<210> SEQ ID NO 54
<211> LENGTH: 62
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
    Asp, Gln, Glu, or Lys
<220> FEATURE:
<221> NAME/KEY: MISC_FEATURE
<222> LOCATION: (31)..(32)
<223> OTHER INFORMATION: Xaa are each either Asp or Glu
<220> FEATURE:
<221> NAME/KEY: MISC_FEATURE
<222> LOCATION: (35)..(39)
<223> OTHER INFORMATION: Xaa are each optionally present and may be
    drawn from the group Ala, Asn, Gln, Gly, Pro, Ser or Thr
<220> FEATURE:
<221> NAME/KEY: MISC_FEATURE
<222> LOCATION: (49)..(49)
<223> OTHER INFORMATION: Xaa is chosen from the group Ala, Arg, Gln,
    Glu, or Lys
<220> FEATURE:
<221> NAME/KEY: MISC_FEATURE
<222> LOCATION: (54)..(54)
<223> OTHER INFORMATION: Xaa is chosen from the group Ala, Arg, Glu,
    Lys, or Pro
<220> FEATURE:
<221> NAME/KEY: MISC_FEATURE
<222> LOCATION: (55)..(55)
<223> OTHER INFORMATION: Xaa is chosen from the group Gln, Glu, Phe,
    Trp, or Tyr

<400> SEQUENCE: 54

Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Pro Thr Xaa Xaa
            20                  25                  30

Gly Pro Xaa Xaa Xaa Xaa Xaa Arg Arg Gly Ile Val Glu Gln Cys Cys
        35                  40                  45

Xaa Ser Ile Cys Ser Xaa Xaa Gln Leu Glu Asn Tyr Cys Asn
50                  55                  60

<210> SEQ ID NO 55
<211> LENGTH: 62
<212> TYPE: PRT
<213> ORGANISM: Homo sapiens
<220> FEATURE:
<221> NAME/KEY: MISC_FEATURE
<222> LOCATION: (29)..(29)
<223> OTHER INFORMATION: Xaa is chosen from the group Ala, Arg, Asn,
    Asp, Gln, Glu, or Lys
<220> FEATURE:

```
<221> NAME/KEY: MISC_FEATURE
<222> LOCATION: (31)..(32)
<223> OTHER INFORMATION: Xaa are each either Asp or Glu
<220> FEATURE:
<221> NAME/KEY: MISC_FEATURE
<222> LOCATION: (35)..(39)
<223> OTHER INFORMATION: Xaa are each optionally present and may be
      drawn from the group Ala, Asn, Gln, Gly, Pro, Ser or Thr
<220> FEATURE:
<221> NAME/KEY: MISC_FEATURE
<222> LOCATION: (49)..(49)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (55)..(55)
<223> OTHER INFORMATION: Xaa is chosen from the group Gln, Glu, Phe,
      Trp, or Tyr

<400> SEQUENCE: 55

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Xaa Thr Xaa Xaa
            20                  25                  30

Gly Pro Xaa Xaa Xaa Xaa Xaa Arg Arg Gly Ile Val Glu Gln Cys Cys
        35                  40                  45

Xaa Ser Ile Cys Ser Leu Xaa Gln Leu Glu Asn Tyr Cys Asn
    50                  55                  60

<210> SEQ ID NO 56
<211> LENGTH: 62
<212> TYPE: PRT
<213> ORGANISM: Homo sapiens
<220> FEATURE:
<221> NAME/KEY: MISC_FEATURE
<222> LOCATION: (29)..(29)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (31)..(32)
<223> OTHER INFORMATION: Xaa are each either Asp or Glu
<220> FEATURE:
<221> NAME/KEY: MISC_FEATURE
<222> LOCATION: (35)..(39)
<223> OTHER INFORMATION: Xaa are each optionally present and may be
      drawn from the group Ala, Asn, Gln, Gly, Pro, Ser or Thr
<220> FEATURE:
<221> NAME/KEY: MISC_FEATURE
<222> LOCATION: (49)..(49)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (55)..(55)
<223> OTHER INFORMATION: Xaa is chosen from the group Gln, Glu, Phe,
      Trp, or Tyr

<400> SEQUENCE: 56

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Xaa Thr Xaa Xaa
            20                  25                  30

Gly Pro Xaa Xaa Xaa Xaa Xaa Arg Arg Gly Ile Val Glu Gln Cys Cys
        35                  40                  45

Xaa Ser Ile Cys Ser Leu Xaa Gln Leu Glu Asn Tyr Cys Asn
    50                  55                  60

<210> SEQ ID NO 57
```

```
<211> LENGTH: 62
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (31)..(32)
<223> OTHER INFORMATION: Xaa are each either Asp or Glu
<220> FEATURE:
<221> NAME/KEY: MISC_FEATURE
<222> LOCATION: (35)..(39)
<223> OTHER INFORMATION: Xaa are each optionally present and may be
      drawn from the group Ala, Asn, Gln, Gly, Pro, Ser or Thr
<220> FEATURE:
<221> NAME/KEY: MISC_FEATURE
<222> LOCATION: (49)..(49)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (55)..(55)
<223> OTHER INFORMATION: Xaa is chosen from the group Gln, Glu, Phe,
      Trp, or Tyr

<400> SEQUENCE: 57

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Xaa Pro Thr Xaa Xaa
                20                  25                  30

Gly Pro Xaa Xaa Xaa Xaa Xaa Arg Arg Gly Ile Val Glu Gln Cys Cys
            35                  40                  45

Xaa Ser Ile Cys Ser Leu Xaa Gln Leu Glu Asn Tyr Cys Asn
 50                  55                  60

<210> SEQ ID NO 58
<211> LENGTH: 59
<212> TYPE: PRT
<213> ORGANISM: Homo sapiens
<220> FEATURE:
<221> NAME/KEY: MISC_FEATURE
<222> LOCATION: (26)..(26)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (28)..(29)
<223> OTHER INFORMATION: Xaa are each either Asp or Glu
<220> FEATURE:
<221> NAME/KEY: MISC_FEATURE
<222> LOCATION: (32)..(36)
<223> OTHER INFORMATION: Xaa are each optionally present and may be
      drawn from the group Ala, Asn, Gln, Gly, Pro, Ser or Thr
<220> FEATURE:
<221> NAME/KEY: MISC_FEATURE
<222> LOCATION: (46)..(46)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (52)..(52)
<223> OTHER INFORMATION: Xaa is chosen from the group Gln, Glu, Phe,
      Trp, or Tyr

<400> SEQUENCE: 58

Gln His Leu Cys Gly Ser His Leu Val Glu Ala Leu Tyr Leu Val Cys
 1               5                  10                  15

Gly Glu Arg Gly Phe Phe Tyr Thr Pro Xaa Thr Xaa Xaa Gly Pro Xaa
                20                  25                  30
```

-continued

```
Xaa Xaa Xaa Xaa Arg Arg Gly Ile Val Glu Gln Cys Cys Xaa Ser Ile
        35                  40                  45

Cys Ser Leu Xaa Gln Leu Glu Asn Tyr Cys Asn
        50                  55

<210> SEQ ID NO 59
<211> LENGTH: 62
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (31)..(32)
<223> OTHER INFORMATION: Xaa are each either Asp or Glu
<220> FEATURE:
<221> NAME/KEY: MISC_FEATURE
<222> LOCATION: (35)..(39)
<223> OTHER INFORMATION: Xaa are each optionally present and may be
      drawn from the group Ala, Asn, Gln, Gly, Pro, Ser or Thr
<220> FEATURE:
<221> NAME/KEY: MISC_FEATURE
<222> LOCATION: (49)..(49)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (55)..(55)
<223> OTHER INFORMATION: Xaa is chosen from the group Gln, Glu, Phe,
      Trp, or Tyr

<400> SEQUENCE: 59

Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Pro Thr Xaa Xaa
                20                  25                  30

Gly Pro Xaa Xaa Xaa Xaa Xaa Arg Arg Gly Ile Val Glu Gln Cys Cys
        35                  40                  45

Xaa Ser Ile Cys Ser Leu Xaa Gln Leu Glu Asn Tyr Cys Asn
        50                  55                  60

<210> SEQ ID NO 60
<211> LENGTH: 61
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (31)..(32)
<223> OTHER INFORMATION: Xaa are each either Asp or Glu
<220> FEATURE:
<221> NAME/KEY: MISC_FEATURE
<222> LOCATION: (34)..(38)
<223> OTHER INFORMATION: Xaa are each optionally present and may be
      drawn from the group Ala, Asn, Gln, Gly, Pro, Ser or Thr
<220> FEATURE:
<221> NAME/KEY: MISC_FEATURE
<222> LOCATION: (48)..(48)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (54)..(54)
<223> OTHER INFORMATION: Xaa is chosen from the group Gln, Glu, Phe,
```

Trp, or Tyr

<400> SEQUENCE: 60

Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Pro Thr Xaa Xaa
            20                  25                  30

Gly Xaa Xaa Xaa Xaa Xaa Arg Arg Gly Ile Val Glu Gln Cys Cys Xaa
        35                  40                  45

Ser Ile Cys Ser Leu Xaa Gln Leu Glu Asn Tyr Cys Asn
    50                  55                  60

<210> SEQ ID NO 61
<211> LENGTH: 60
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (31)..(32)
<223> OTHER INFORMATION: Xaa are each either Asp or Glu
<220> FEATURE:
<221> NAME/KEY: MISC_FEATURE
<222> LOCATION: (33)..(37)
<223> OTHER INFORMATION: Xaa are each optionally present and may be
      drawn from the group Ala, Asn, Gln, Gly, Pro, Ser or Thr
<220> FEATURE:
<221> NAME/KEY: MISC_FEATURE
<222> LOCATION: (47)..(47)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (53)..(53)
<223> OTHER INFORMATION: Xaa is chosen from the group Gln, Glu, Phe,
      Trp, or Tyr

<400> SEQUENCE: 61

Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Pro Thr Xaa Xaa
            20                  25                  30

Xaa Xaa Xaa Xaa Xaa Arg Arg Gly Ile Val Glu Gln Cys Cys Xaa Ser
        35                  40                  45

Ile Cys Ser Leu Xaa Gln Leu Glu Asn Tyr Cys Asn
    50                  55                  60

<210> SEQ ID NO 62
<211> LENGTH: 59
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (31)..(32)
<223> OTHER INFORMATION: Xaa are each either Asp or Glu
<220> FEATURE:
<221> NAME/KEY: MISC_FEATURE
<222> LOCATION: (33)..(37)
<223> OTHER INFORMATION: Xaa are each optionally present and may be
      drawn from the group Ala, Asn, Gln, Gly, Pro, Ser or Thr

```
<220> FEATURE:
<221> NAME/KEY: MISC_FEATURE
<222> LOCATION: (46)..(46)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (52)..(52)
<223> OTHER INFORMATION: Xaa is chosen from the group Gln, Glu, Phe,
      Trp, or Tyr

<400> SEQUENCE: 62

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Xaa Pro Thr Xaa Xaa
             20                  25                  30

Xaa Xaa Xaa Xaa Xaa Arg Gly Ile Val Glu Gln Cys Cys Xaa Ser Ile
         35                  40                  45

Cys Ser Leu Xaa Gln Leu Glu Asn Tyr Cys Asn
         50                  55

<210> SEQ ID NO 63
<211> LENGTH: 62
<212> TYPE: PRT
<213> ORGANISM: Homo sapiens
<220> FEATURE:
<221> NAME/KEY: MISC_FEATURE
<222> LOCATION: (29)..(29)
<223> OTHER INFORMATION: Xaa is chosen from the group Ala, Arg, Asn,
      Asp, Gln, Glu, or Lys
<220> FEATURE:
<221> NAME/KEY: MISC_FEATURE
<222> LOCATION: (31)..(32)
<223> OTHER INFORMATION: Xaa are each either Asp or Glu
<220> FEATURE:
<221> NAME/KEY: MISC_FEATURE
<222> LOCATION: (35)..(39)
<223> OTHER INFORMATION: Xaa are each optionally present and may be
      drawn from the group Ala, Asn, Gln, Gly, Pro, Ser or Thr
<220> FEATURE:
<221> NAME/KEY: MISC_FEATURE
<222> LOCATION: (49)..(49)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (55)..(55)
<223> OTHER INFORMATION: Xaa is chosen from the group Gln, Glu, Phe,
      Trp, or Tyr

<400> SEQUENCE: 63

Phe Val Asn Gln His Leu Cys Gly Ser His Leu Val Gln Ala Leu Tyr
 1               5                  10                  15

Leu Val Cys Gly Glu Arg Gly Phe Phe Tyr Thr Pro Xaa Thr Xaa Xaa
             20                  25                  30

Gly Pro Xaa Xaa Xaa Xaa Xaa Arg Arg Gly Ile Val Glu Gln Cys Cys
         35                  40                  45

Xaa Ser Ile Cys Ser Leu Xaa Gln Leu Glu Asn Tyr Cys Asn
         50                  55                  60

<210> SEQ ID NO 64
<211> LENGTH: 59
<212> TYPE: PRT
<213> ORGANISM: Homo sapiens
<220> FEATURE:
<221> NAME/KEY: MISC_FEATURE
<222> LOCATION: (25)..(25)
<223> OTHER INFORMATION: Xaa is chosen from the group Ala, Arg, Asn,
      Asp, Gln, Glu, or Lys
```

<220> FEATURE:
<221> NAME/KEY: MISC_FEATURE
<222> LOCATION: (28)..(29)
<223> OTHER INFORMATION: Xaa are each either Asp or Glu
<220> FEATURE:
<221> NAME/KEY: MISC_FEATURE
<222> LOCATION: (32)..(36)
<223> OTHER INFORMATION: Xaa are each optionally present and may be
      drawn from the group Ala, Asn, Gln, Gly, Pro, Ser or Thr
<220> FEATURE:
<221> NAME/KEY: MISC_FEATURE
<222> LOCATION: (46)..(46)
<223> OTHER INFORMATION: Xaa is chosen from the group Ala, Arg, Gln,
      Glu, or Lys
<220> FEATURE:
<221> NAME/KEY: MISC_FEATURE
<222> LOCATION: (52)..(52)
<223> OTHER INFORMATION: Xaa is chosen from the group Gln, Glu, Phe,
      Trp, or Tyr

<400> SEQUENCE: 64

Gln His Leu Cys Gly Ser His Leu Val Glu Ala Leu Tyr Leu Val Cys
1               5                   10                  15

Gly Glu Arg Gly Phe Phe Tyr Thr Xaa Pro Thr Xaa Xaa Gly Pro Xaa
            20                  25                  30

Xaa Xaa Xaa Xaa Arg Arg Gly Ile Val Glu Gln Cys Cys Xaa Ser Ile
        35                  40                  45

Cys Ser Leu Xaa Gln Leu Glu Asn Tyr Cys Asn
    50                  55

<210> SEQ ID NO 65
<211> LENGTH: 174
<212> TYPE: DNA
<213> ORGANISM: Homo sapiens

<400> SEQUENCE: 65
ttcgtcaatc aacacttgtg tggttcccac ttggttgagg cattgtactt ggtctgtggt    60
gagagaggat tcttctacac cgatccaact ggtggtggtc ctagaagagg aatcgtcgag   120
caatgttgcc actccatttg ttccttggaa caattggaaa actactgcaa ctaa          174

<210> SEQ ID NO 66
<211> LENGTH: 174
<212> TYPE: DNA
<213> ORGANISM: Homo sapiens

<400> SEQUENCE: 66
ttcgtcaatc aacacttgtg tggttcccac ttggttgagg cattgtactt ggtctgtggt    60
gagagaggat tcttctacac cgatccaact ggtgagggtc ctagaagagg aatcgtcgag   120
caatgttgcc actccatttg ttccttggaa caattggaaa actactgcaa ctaa          174

<210> SEQ ID NO 67
<211> LENGTH: 174
<212> TYPE: DNA
<213> ORGANISM: Homo sapiens

<400> SEQUENCE: 67
ttcgtcaatc agcacttgtg tggttcccac ttggttgagg ctttgtactt ggtttgtggt    60
gagagaggtt tcttctacac tgatccaact gaagagggtc caagaagagg tatcgttgag   120
cagtgttgtc actccatctg ttccttggag cagttggaga actactgtaa ctga          174

<210> SEQ ID NO 68
<211> LENGTH: 174

<212> TYPE: DNA
<213> ORGANISM: Homo sapiens

<400> SEQUENCE: 68
ttcgtcaatc agcacttgtg tggttcccac ttggttgagg ctttgtactt ggtttgtggt    60
gagagaggtt tcttctacac tgatccaact gaagagggtc caagaagagg tatcgttgag   120
cagtgttgtc actccatctg ttcctgggag cagttggaga actactgtaa ctga         174

<210> SEQ ID NO 69
<211> LENGTH: 174
<212> TYPE: DNA
<213> ORGANISM: Homo sapiens

<400> SEQUENCE: 69
ttcgtcaatc agcacttgtg tggttcccac ttggttgagg ctttgtactt ggtttgtggt    60
gagagaggtt tcttctacac tccagaaact gaagagggtc caagaagagg tatcgttgag   120
cagtgttgtc actccatctg ttccttggag cagttggaga actactgtaa ctga         174

<210> SEQ ID NO 70
<211> LENGTH: 174
<212> TYPE: DNA
<213> ORGANISM: Homo sapiens

<400> SEQUENCE: 70
ttcgtcaatc agcacttgtg tggttcccac ttggttgagg ctttgtactt ggtttgtggt    60
gagagaggtt tcttctacac tccaagaact gaagagggtc caagaagagg tatcgttgag   120
cagtgttgtc actccatctg ttccttggag cagttggaga actactgtaa ctga         174

<210> SEQ ID NO 71
<211> LENGTH: 174
<212> TYPE: DNA
<213> ORGANISM: Homo sapiens

<400> SEQUENCE: 71
ttcgtcaatc agcacttgtg tggttcccac ttggttgagg ctttgtactt ggtttgtggt    60
gagagaggtt tcttctacac tgagccaact gaagagggtc caagaagagg tatcgttgag   120
cagtgttgtc actccatctg ttccttggag cagttggaga actactgtaa ctga         174

<210> SEQ ID NO 72
<211> LENGTH: 174
<212> TYPE: DNA
<213> ORGANISM: Homo sapiens

<400> SEQUENCE: 72
ttcgtcaaac agcacttgtg tggttcccac ttggttgagg ctttgtactt ggtttgtggt    60
gagagaggtt tcttctacac tccagaaact gaagagggtc caagaagagg tatcgttgag   120
cagtgttgtc actccatctg ttccttggag cagttggaga actactgtaa ctga         174

<210> SEQ ID NO 73
<211> LENGTH: 168
<212> TYPE: DNA
<213> ORGANISM: Homo sapiens

<400> SEQUENCE: 73
ttcgttaacc agcacttgtg tggttcccac ttggttgagg ctttgtactt ggtttgtggt    60
gagagaggtt tcttctacac tgatccaact gaagagagaa gaggtatcgt tgagcagtgt   120

-continued

```
tgtcactcca tctgttcctt ggagcagttg gagaactact gtaactaa          168

<210> SEQ ID NO 74
<211> LENGTH: 168
<212> TYPE: DNA
<213> ORGANISM: Homo sapiens

<400> SEQUENCE: 74
ttcgttaacc agcacttgtg tggttcccac ttggttgagg ctttgtactt ggtttgtggt    60
gagagaggtt tcttctacac tgatccaact gaagagagaa gaggtatcgt tgagcagtgt   120
tgtcactcca tctgttcctt ggagcagttg gagaactact gtaactaa              168

<210> SEQ ID NO 75
<211> LENGTH: 165
<212> TYPE: DNA
<213> ORGANISM: Homo sapiens

<400> SEQUENCE: 75
ttcgttaacc agcacttgtg tggttcccac ttggttgagg ctttgtactt ggtttgtggt    60
gagagaggtt tcttctacac tgatccaact gaagagagag gtatcgttga gcagtgttgt   120
cactccatct gttccttgga gcagttggag aactactgta actaa                  165

<210> SEQ ID NO 76
<211> LENGTH: 174
<212> TYPE: DNA
<213> ORGANISM: Homo sapiens

<400> SEQUENCE: 76
ttcgtcaatc agcacttgtg tggttcccac ttggttcagg ctttgtactt ggtttgtggt    60
gagagaggtt tcttctacac tccagaaact gaagagggtc caagaagagg tatcgttgag   120
cagtgttgtc actccatctg ttccttggag cagttggaga actactgtaa ctga         174

<210> SEQ ID NO 77
<211> LENGTH: 174
<212> TYPE: DNA
<213> ORGANISM: Homo sapiens

<400> SEQUENCE: 77
ttcgtcaaac agcacttgtg tggttcccac ttggttgagg ctttgtactt ggtttgtggt    60
gagagaggtt tcttctacac tgacccaact gaagagggtc caagaagagg tatcgttgag   120
cagtgttgtc actccatctg ttccttggag cagttggaga actactgtaa ctga         174
```

BIPHASIC SINGLE-CHAIN INSULIN ANALOGUES

STATEMENT REGARDING FEDERALLY SPONSORED RESEARCH OR DEVELOPMENT

This invention was made with government support under grant numbers DK040949 and DK074176 awarded by the National Institutes of Health. The U.S. government has certain rights in the invention.

CROSS REFERENCE TO RELATED APPLICATIONS

This application is a national stage application of PCT/US2015/054263 which was filed on Oct. 6, 2015, which is a non-provisional of U.S. Patent Application No. 62/060,167 which was filed on Oct. 6, 2014, the disclosures of which are incorporated by reference herein.

BACKGROUND OF THE INVENTION

This invention relates to polypeptide hormone analogues that exhibits enhanced pharmaceutical properties, such as increased increased thermodynamic stability, augmented resistance to thermal fibrillation above room temperature, decreased mitogenicity, and/or altered pharmacokinetic and pharmacodynamic properties, i.e., conferring a biphasic time course of action relative to (a) a fast-acting component similar to soluble formulations of the corresponding prandial or wild-type human hormone and (b) a prolonged component similar to microcrystalline NPH formulations of wild-type insulin or insulin analogues. More particularly, this invention relates to insulin analogues consisting of a single polypeptide chain that (i) contains a novel class of foreshortened connecting (C) domains between A and B domains with acidic residues at the first and second positions, (ii) contains an amino-acid substitution at position A8, and (iii) contains an acidic residue at position A14. Of length 6-11 residues, the C domains of this class consist of an N-terminal acidic element and a C-terminal segment basic element similar to that of wild-type proinsulin. The single-chain insulina analogues of the present invention may optionally contain standard or non-standard amino-acid substitutions at other sites in the A or B domains, such as positions B28 and B29 known in the art to confer rapid action.

The engineering of non-standard proteins, including therapeutic agents and vaccines, may have broad medical and societal benefits. Naturally occurring proteins—as encoded in the genomes of human beings, other mammals, vertebrate organisms, invertebrate organisms, or eukaryotic cells in general—often confer multiple biological activities. A benefit of non-standard proteins would be to achieve selective activity, such as decreased binding to homologous cellular receptors associated with an unintended and unfavorable side effect, such as promotion of the growth of cancer cells. Yet another example of a societal benefit would be augmented resistance to degradation at or above room temperature, facilitating transport, distribution, and use. An example of a therapeutic protein is provided by insulin. Wild-type human insulin and insulin molecules encoded in the genomes of other mammals bind to insulin receptors in multiple organs and diverse types of cells, irrespective of the receptor isoform generated by alternative modes of RNA splicing or by alternative patterns of post-translational glycosylation. Wild-type insulin also binds with lower affinity to the homologous Type 1 insulin-like growth factor receptor (IGF-1R).

An example of a further medical benefit would be optimization of the pharmacokinetic properties of a soluble formulation such that the time course of insulin action has two phases, a rapid phase and a delayed phase (FIG. 1). Such a combination of rapid and delayed phases is known in the art to be conferred by mixtures of a solution of zinc insulin analogue hexamers (as provided by, but not limited to, insulin lispro and insulin aspart) with a micro-crystalline suspension of the same analogue prepared in combination with zinc ions and protamines or protamine-related basic peptides; the latter component is designated in the art as Neutral Protamine Hagedorn (NPH) micro-crystalline suspensions. Pre-mixed insulin products known in the art contain varying ratios of these two components, such as 25% soluble phase and 75% micro-crystalline phase, 30% soluble phase and 70% micro-crystalline phase, or 50% of each phase. Such pre-mixed products are widely used by patients with diabetes mellitus in the developing world due to their ease of use with reduction in the number of subcutaneous injections per day relative to the separate administration of a prandial (rapid-acting) insulin formulation (or prandial insulin analogue formulation) and of a NPH micro-crystalline suspension of wild-type insulin or insulin analogue. The simplification of insulin regimens of insulin provided by pre-mixed biphasic insulin products has also proven of benefit to patients with diabetes mellitus in affluent societies (i) for whom treatment solely by prandial insulin analogue formulations leads to suboptimal glycemic control or excessive weight gain, (ii) for whom treatment solely by NPH insulin products or basal insulin analog formulations leads to suboptimal glycemic control due to upward excursions in the blood glucose concentration within three hours after a meal, or (iii) patients of the above two classes for whom addition of an oral agent (such as metformin) does not result in satisfactory glycemic control.

Existing biphasic insulin products require a complex and costly method of manufacture due to the post-fermentation and post-purification steps needed to grow NPH micro-crystals. Further, such products suffer from an intrinsic susceptibility of both the soluble and micro-crystalline components to physical and chemical degradation above room temperature. The biphasic pharmacokinetic properties of these pre-mixed products may change with storage of the vials above room temperature due to interchange of insulin molecules between the soluble and micro-crystalline phases. Finally, the use of micro-crystalline suspensions can be associated with uncertainties in dosing as the number of micro-crystals drawn into a syringe can vary from withdrawal to withdrawal even from the same vial.

In light of the above disadvantages of existing biphasic insulin products, the therapeutic and societal benefits of biphasic insulin formulations would be enhanced by the engineering of insulin analogues whose pharmacokinetic properties as a mono-component soluble solution confer a biphasic pattern of insulin action. Additional benefits would accrue if the novel soluble insulin analogue were simpler and less costly to manufacture (i.e., by avoiding the requirement for micro-crystallization) and/or if the novel soluble insulin analogue were more refractory than wild-type insulin to chemical or physical degradation at or above room temperature. Such resistance to degradation above room temperature would be expected to facilitate use in regions of the developing world where electricity and refrigeration are not consistently available. The challenge posed by such degradation is deepened by the pending pandemic of diabetes mellitus in Africa and Asia. Because fibrillation poses the major route of degradation above room temperature, the design of fibrillation-resistant formulations may enhance the safety and efficacy of insulin replacement therapy in such challenged regions. Still additional therapeutic and societal benefit would accrue if the soluble biphasic insulin analogue should exhibit reduced mitogenicity in assays developed to monitor insulin-stimulated proliferation of human cancer cell lines.

Administration of insulin has long been established as a treatment for diabetes mellitus. A major goal of conventional insulin replacement therapy in patients with diabetes mellitus is tight control of the blood glucose concentration to prevent its excursion above or below the normal range characteristic of healthy human subjects. Excursions below the normal range are associated with immediate adrenergic or neuroglycopenic symptoms, which in severe episodes lead to convulsions, coma, and death. Excursions above the normal range are associated with increased long-term risk of microvascular disease, including retinapathy, blindness, and renal failure. Insulin is a small globular protein that plays a central role in metabolism in vertebrates. Insulin contains two chains, an A chain, containing 21 residues, and a B chain containing 30 residues. The hormone is stored in the pancreatic-cell as a $Zn^{2+}$-stabilized hexamer, but functions as a $Zn^{2+}$-free monomer in the bloodstream. Insulin is the product of a single-chain precursor, proinsulin, in which a connecting region (35 residues) links the C-terminal residue of B chain (residue B30) to the N-terminal residue of the A chain. A variety of evidence indicates that it consists of an insulin-like core and disordered connecting peptide. Formation of three specific disulfide bridges (A6-A11, A7-B7, and A20-B19) is thought to be coupled to oxidative folding of proinsulin in the rough endoplasmic reticulum (ER). Proinsulin assembles to form soluble $Zn^{2+}$-coordinated hexamers shortly after export from ER to the Golgi apparatus. Endoproteolytic digestion and conversion to insulin occurs in immature secretory granules followed by morphological condensation. Crystalline arrays of zinc insulin hexamers within mature storage granules have been visualized by electron microscopy (EM). Individual residues are indicated by the identity of the amino acid (typically using a standard three-letter code), the chain and sequence position (typically as a superscript). Pertinent to the present invention is the invention of novel foreshortened C domains of length 6-11 residues, containing an N-terminal acidic motif and a C-terminal basic motif, in place of the 36-residue wild-type C domain characteristic of human proinsulin and in combination with amino-acid substitutions at positions A8 and A14 of the A chain and optionally at positions B28 and B29 of the B chain.

Fibrillation, which is a serious concern in the manufacture, storage and use of insulin and insulin analogues for the treatment of diabetes mellitus, is enhanced with higher temperature, lower pH, agitation, or the presence of urea, guanidine, ethanol co-solvent, or hydrophobic surfaces. Current US drug regulations demand that insulin be discarded if fibrillation occurs at a level of one percent or more. Because fibrillation is enhanced at higher temperatures, patients with diabetes mellitus optimally must keep insulin refrigerated prior to use. Insulin exhibits an increase in degradation rate of 10-fold or more for each 10° C. increment in temperature above 25° C.; accordingly, guidelines call for storage at temperatures <30° C. and preferably with refrigeration. The NPH micro-crystalline component of existing biphasic insulin product is susceptible to fibrillation above room temperature as well as a distinctive mode of chemical degradation due to proteolytic cleavage within the A chain; such cleavage inactivates the insulin or insulin analogue.

The above cleavage of the insulin A chain in NPH micro-crystals is representative of a process involving the breakage of chemical bonds. Such breakage can lead to loss or rearrangement of atoms within the insulin molecule or the formation of chemical bonds between different insulin molecules, leading to formation of polymers. Whereas cleavage of the A chain in NPH micro-crystals is thought to occur on the surface of the folded state, other changes in chemical bonds are mediated in the unfolded state of the protein or in partially unfolded forms of the protein, and so modifications of insulin that augment its thermodynamic stability also are likely to delay or prevent chemical degradation. It is therefore a desirable property of an insulin analogue that its free energy of denaturation (as typically measured by circular dichroism at a helix-sensitive wavelength as a function of the concentration of a chemical denaturant) should be equal to or greater than that of wild-type insulin or equal to or greater than that of a prandial (rapid-acting) insulin analogue in current clinical use.

Insulin is also susceptible to physical degradation. The present theory of protein fibrillation posits that the mechanism of fibrillation proceeds via a partially folded intermediate state, which in turn aggregates to form an amyloidogenic nucleus. In this theory, it is possible that amino-acid substitutions that stabilize the native state may or may not stabilize the partially folded intermediate state and may or may not increase (or decrease) the free-energy barrier between the native state and the intermediate state. Therefore, the current theory indicates that the tendency of a given amino-acid substitution in the two-chain insulin molecule to increase or decrease the risk of fibrillation is highly unpredictable. Models of the structure of the insulin molecule envisage near-complete unfolding of the three alpha-helices (as seen in the native state) with parallel arrangements of beta-sheets forming successive stacking of B-chains and successive stacking of A-chains; native disulfide pairing between chains and within the A-chain is retained. Such parallel cross-beta sheets require substantial separation between the N-terminus of the A-chain and C-terminus of the B-chain (>30 Å), termini ordinarily in close proximity in the native state of the insulin monomer (<10 Å). Marked resistance to fibrillation of single-chain insulin analogues with foreshortened C-domains is known in the art and thought to reflect a topological incompatibility between the splayed structure of parallel cross-beta sheets in an insulin protofilament and the structure of a single-chain insulin analogue with native disulfide pairing in which the foreshortened C-domain constrains the distance between the N-terminus of the A-chain and C-terminus of the B-chain to be unfavorable in a protofilament. A ribbon model of a single-chain insulin analogue is shown in FIG. 2; a space-filling model of the insulin moiety is shown in FIG. 3 to highlight the role of the engineered connecting domain (C domain; stick representation in FIG. 3).

The present invention was motivated by the medical and societal needs to engineer a biphasic single-chain insulin analogue in a soluble and monophasic formulation at neutral pH intended for twice-a-day injection, i.e., on a schedule similar to that of current pre-mixed regular-NPH biphasic insulin products. Our single-chain design is intended to combine (i) resistance to degradation with (ii) substantial in vivo hypoglycemic potency with (iii) reduced cross-binding to IGF-1R and (iv) intrinsic biphasic pharmacokinetics and pharmacodynamics in the absence of a component consisting of a micro-crystalline suspension. It would be desirable, therefore, to invent single-chain insulin analogue that, as a soluble protein solution at neutral pH, exhibits biphasic pharmacokinetic- and pharmacodynamics properties on subcutaneous injection such that both rapid-onset of action and a prolonged tail of action are achieved leading to an overall profile that resembles those of premixed products as exemplied by "Humalog® Mix75/25" or "NovaMix® 30." Biphasic insulin analog formulations of the present invention will therefore provide simplified twice-a-day bolus-basal regimens that will be of clinical advantage in the developed and developing world. Single-chain biphasic insulin analogue formulations may also be initiated in insulin-naïve patients not well controlled on metformin, a first-line oral agent widely used in the treatment of T2DM. The mechanism of biphasic action of current regular-NPH premixed products, based on pharmacokinetic properties of the two components, is shown in schematic form in FIG. 4A. While not wishing to be constrained by theory, a possible mechanism of biphasic pharmacokinetics by analogies of the present invention is shown in schematic form in FIG. 4B.

We envisage that the products of the present invention will disproportionately benefits patients in Western societies whose compliance with more complex regimens is uncertain. It is known in the art that health-care outcomes—and long-term adherence to prescribed regimens in chronic diseases such as T2DM and the metabolic syndrome—are a complex function of socioeconomic status, formal education, family structure, and cultural belief systems. Indeed, these societal issues are of increasing concern given the growing burden of obesity and T2DM among under-represented minorities, including African-Americans, Hispanic and indigenous Americans. Single-chain biphasic insulin analogue formulations of the present invention are therefore intended to benefit insulin-requiring T1DM and T2DM patients who have inadequate glycemic control with basal-only insulin therapy but for whom a full basal-bolus regimen is impractical.

SUMMARY OF THE INVENTION

It is, therefore, an aspect of the present invention to provide single-chain insulin analogues that provide biphasic pharmacokinetic and pharmacodynamics properties on subcutaneous injection. The analogues of the present invention contain Histidine at position B10 and so circumvent concerns regarding carcinigenesis that is associated with an acidic substitution (Aspartic Acid or Glutamic Acid) at this position. It is an additional aspect of the present invention that absolute in vitro affinities of the single-chain insulin analogue for IR-A and IR-B are in the range 5-100% relative to wild-type human insulin and so unlikely to exhibit prolonged residence times in the hormone-receptor complex.

The above combination of features is conferred by a novel C-domain design wherein a foreshortened connecting polypeptide (length 6-11 residues) contains an N-terminal acidic element (residues C1 and C2), a flexible joint or hinge (C3 and C4), and C-terminal segment containing a pair of basic residues analogous to those observed in natural proinsulins (C5 and C6). An upper limit of 11 for the C-domain length was chosen to be below the 12-residue IGF-I-derived linker described in a chimeric insulin analogue with enhanced IGF-1R-binding activity (Kristensen, C., et al. 1995). A lower limit of 4 was chosen to preserve the acidic motif at the N-terminal portion of the connection domain (such as, but not restricted to, Glu-Glu) and basic motif at the C-terminal portion of the connection domain (such as, but not restricted to, Arg-Arg). Although not wishing to be constrained by theory, we imagine that the two-residue acidic residue introduces unfavorable electrostatic repulsion on binding of the analogue to IGF-1R but is well tolerated by insulin receptor isoforms. Also without wishing to be constrained by theory, we further imagine that the C-terminal basic motif contributes to partial subcutaneous aggregation rather than a mere tether or space element.

In general, the present invention provides a single-chain insulin analogue comprising a C-domain of the present invention and a modified A-chain containing substitutions at position A8 and A14. The present invention thus pertains to a novel class of single-chain insulin analogues wherein the connecting domain (C domain) is of length 4-11 and consists of two elements. The N-terminal element consists of the first two residues (designated C1 and C2, corresponding to residues B31-B32 of an extended insulin B-chain) wherein C1 and C2 contain at least one acidic side chain and a net formal electrostatic charge at pH 7.4 of −1 or −2. The C-terminal element contains two basic residues as Arg-Arg, Lys-Lys, Arg-Lys or Lys-Arg. For four-residue connecting domains, the sequences of the present invention would thus include, but not be limited to, Glu-Glu-Arg-Arg, Glu-Ala-Arg-Arg, Ala-Glu-Arg-Arg, Asp-Glu-Arg-Arg, Glu-Glu-Lys-Arg, Glu-Glu-Arg-Lys, and Glu-Glu-Lys-Lys. Between the N- and C-terminal elements in the case of connecting domains of length greater than 4 (i.e., in the range 5-11), the connection domain contains a flexible joint. In the example of a six-residue connecting domain, such sequences may contain at positions C3 and C4 Gly-Pro, Ser-Pro, Ala, Pro, Gly-Ser, Ser-Ser, Gly-Gly, or Ala-Ala but the scope of the present invention is not limited to these possibilities. The A-chain contains a basic substitution at A8 (Lysine, Arginine, or Histidine) and a substitution at A21 (Gly, Ala, or Ser) to avoid acid-catalyzed deamidation or other modes of Asn-related chemical degradation. In one example the B-chain also contains substitutions Lys$^{B29}$→Arg to avoid Lys-specific proteolytic cleavage in the course of biosynthesis in yeast. The analogues of the present invention also contain a substitution at position A8 (Ala, Glu, Gln, His, Lys, or Arg), intended to enhance stability and activity; and a substitution at A14 (Glu), intended to avoid the reverse-hydrophobic effect presumably incurred by the wild-type TyrA14 and to provide an additional negative charge. Other possible substitutions at position A14 are also envisioned.

purple, electropositive; and white, neutral). This image was obtained from PDB entry 2jzq, based upon NMR studies in the Weiss laboratory (Hua, Q. X., et al. *J. Biol. Chem.* 283, 14703-16 (2008)).

Figure 4:
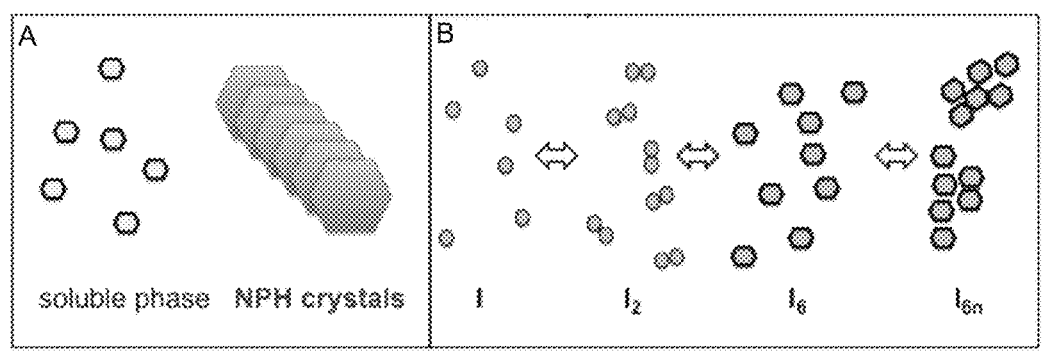

FIG. 4. Old and new paradigms. (A) Current biphasic insulin products contain a soluble phase (zinc hexamers; green) and an insoluble phase (NPH microcrystalline suspension; blue). (B) Proposed new paradigm seeks to exploit coupled equilibria among monomeric insulin analog (I), zinc-free dimer ($I_2$), zinc-stabilized and/or zinc-free hexamers ($I_6$), and soluble aggregates ($I_{6n}$). Not shown: TR transition.

Figure 5:
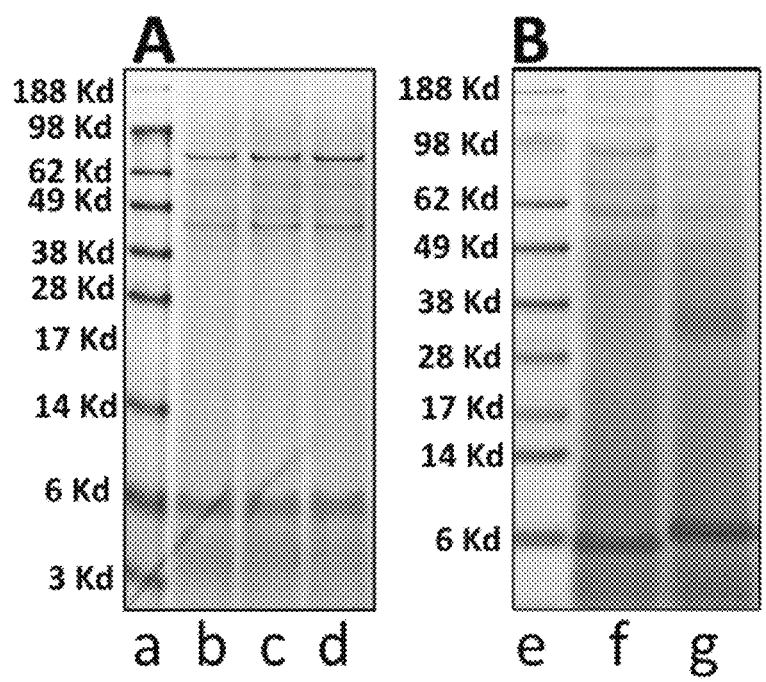

FIG. 5. Over-expression of Thermalin-biphasic (versions 1 and 2) in yeast *P. pastoris*. Coomasie-stained SDS-PAGE gels: (A) SCI-57PE (lanes b-d) relative to molecular-mass markers (a). (B) SCI-57DP (lane g) relative to $His^{48}$-miniproinsulin (MPI) as positive control (f) and standards (e). The SCIs migrate ≈6 kilo-Daltons ($K_d$); mini-proinsulins near 5.8 Kd.

Figure 6:
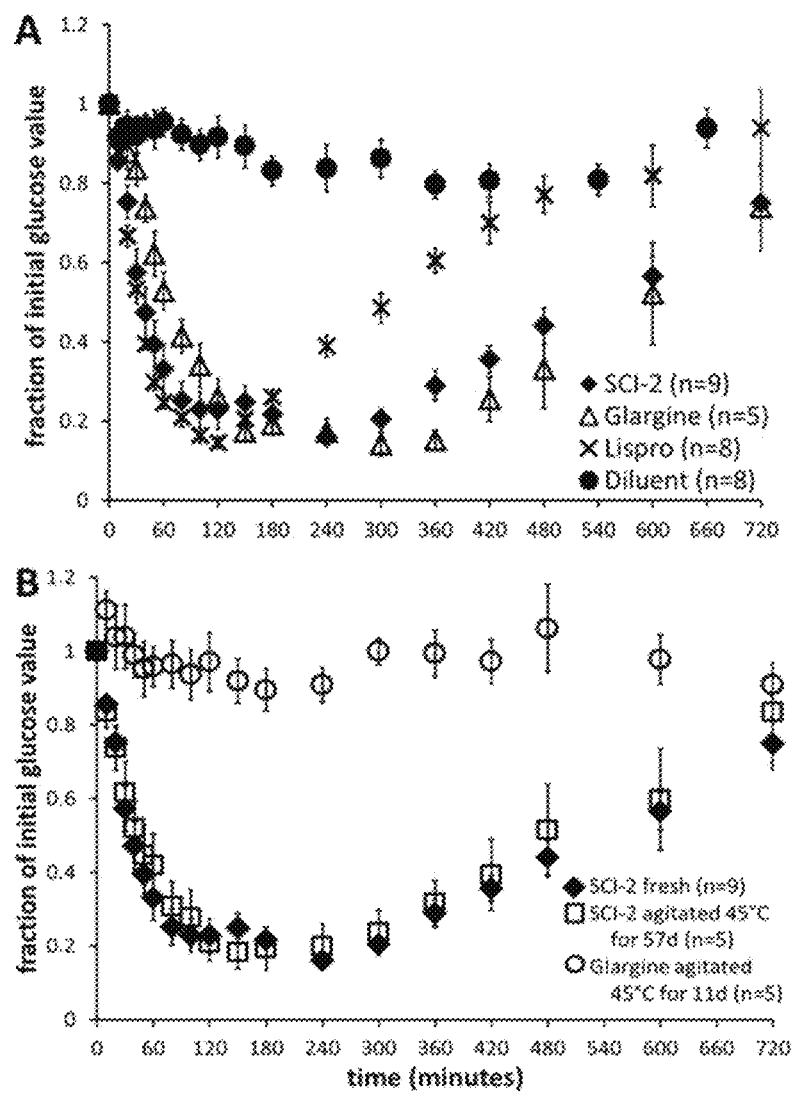

FIG. 6. Diabetic rats (time 0 blood glucose of 400±20 mg/dl) were injected s.q. with 1 unit of the indicated insulin analog/300 g body weight. A. (✶) Humalog (lispro) vs. (Δ) Humalog 25/75-Premix vs. (▲) SCI-57PE (labeled SCI-1 in the figure) fresh vs. (◆) SCI-57DP (labeled SCI-2) fresh vs. (●) diluent. B. Decrease in blood glucose during the first $1^{st}$ hour post-injection (same symbol codes). The number of rats in each group (n) was as indicated; error bars, standard errors.

Figure 7:
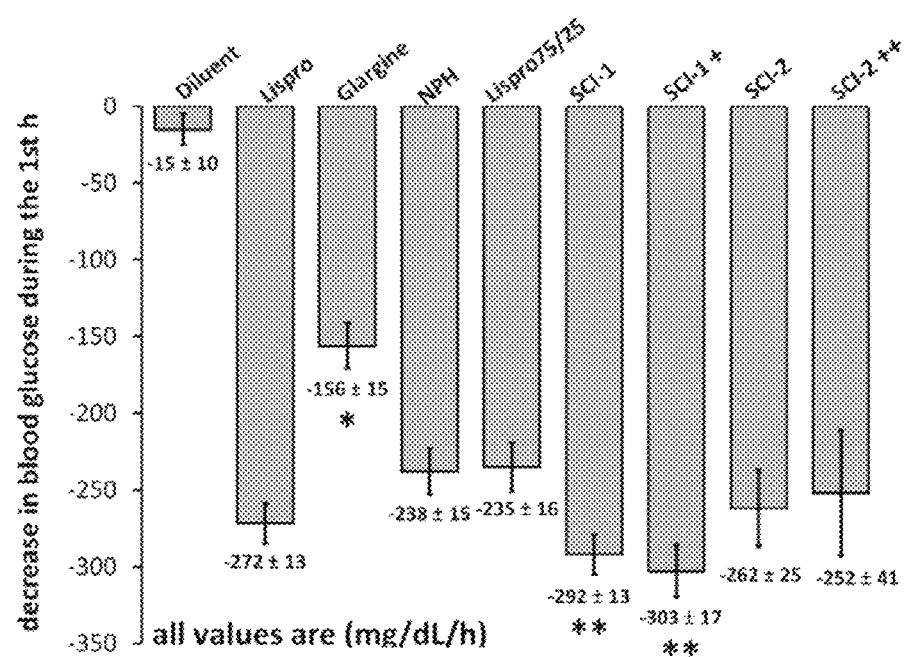

FIG. 7. Initial rate of decrease in [blood glucose] following 1 unit s.q. injection of the indicated insulin analog: + denotes SCI-57PE (labeled SCI-1) agitated at 45° C. for 25 days; ++ denotes SCI-57DP (labeled SCI-2) agitated at 45° C. for 57 days. *$p<0.05$ compared to all other insulin. ** $p<0.05$ compared to pre-mixed Lispro 75/25. Data pertain to first hour post-injection (see FIG. 8B); error bars, standard errors.

Figure 8:
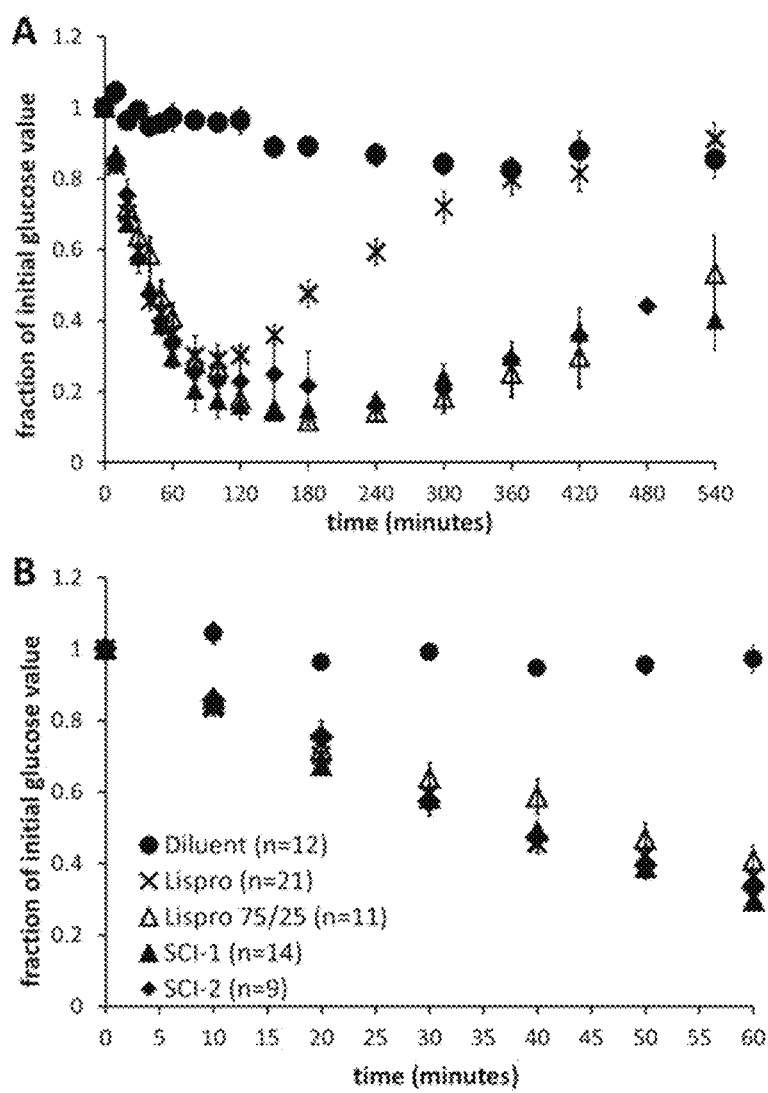

FIG. 8. Diabetic rats (time 0 blood glucose of 410±20 mg/dl) were injected s.q. with 1 unit of the indicated analog/300 g body weight. A. Fresh samples: (◆) SCI-57DP (labeled SCI-2), (Δ) Lantus (glargine), (✶) Humalog (lispro), and (●) diluent. A. Fresh insulin. B. Effects of agitation at high temperature: (◆) fresh SCI-57DP vs. (□) SCI-57DP agitated at 45° C. for 57 days vs. (○) Lantus (glargine) agitated at 45° C. for 11 days.

Figure 9:
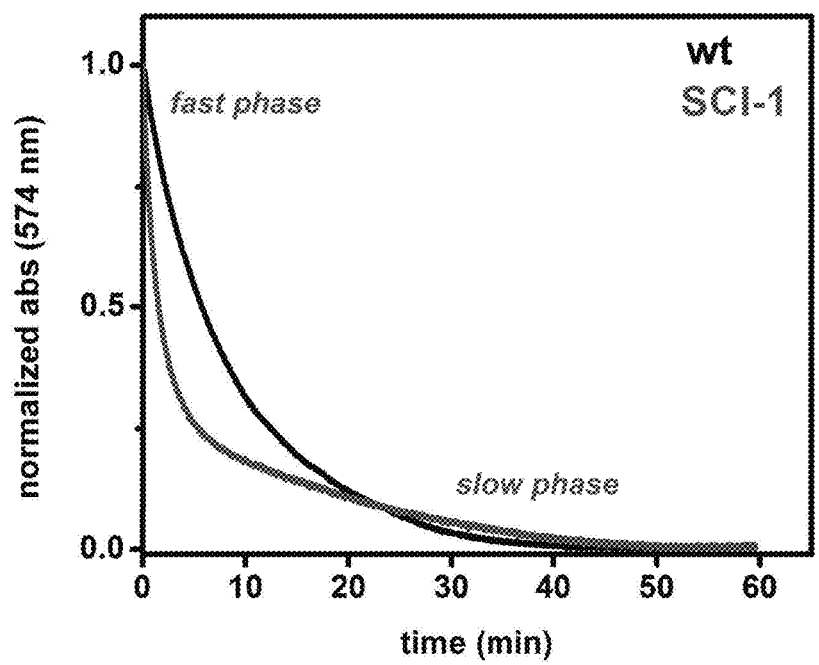

FIG. 9. Lilly $Co^{2+}$-EDTA sequestration assay: normalized absorbance at visible wavelength 574 nm is shown as a function of time following addition of EDTA (in 10-fold molar excess) to a solution of $R_6$ cobalt insulin hexamers or SCI-1 hexamers at 25° C. Wild-type insulin (black line): mono-exponential transition with time constant 6.3 (±0.1) min. SCI-1 (green line): biphasic transition with time constants 0.9 (±0.1) min (fast phase) and 14.1 (±0.1) min (slow phase); $r^2=0.998$. Proteins were 3.5 mg/ml in 50 mM Tris-HCl (pH 7.4) containing 1 mM NaSCN, 0.2 mM $CoCl_2$, and 50 mM phenol.

DETAILED DESCRIPTION OF THE INVENTION

The present invention is directed toward a single-chain insulin analogue that provides protracted duration of action, a ratio of IR-A/IR-B receptor-binding affinities similar to that of wild-type insulin with absolute affinities in the range 5-100% (the lower limit chosen to correspond to proinsulin), increased discrimination against IGF-1R, presumed augmented resistance to chemical degradation at position A21 (due to substitution of Asn by Gly, Ala or Ser), presumed augmented resistance to fibrillation above room temperature (due to single-chain topology), and presumed increased thermodynamic activity (due in part to substitution of $Thr^{48}$ by a basic side chain; Arg, Lys, His, Orn).

It is a feature of the present invention that biphasic absorption kinetics from a subcutaneous depot may be generated by a single-chain insulin analogue when formulated as a clear and soluble monophasic solution of the protein. Conventional premixed products, as known in the art, represent an extreme end of a continuum of possible coupled equilibria between states of self-assembly (FIG. 4A). Alternative strategies to provide a combination of rapid and delayed absorption are envisaged that depend on the rate constants governing these coupled equilibria and relative thermodynamic stabilities as illustrated in schematic form FIG. 4B. Molecular implementation of this strategy requires an insulin analog that is (i) ultra-stable as a zinc-free monomer and dimer and (ii) also amenable to forming stable zinc-mediated hexamers susceptible to higher-order aggregation (soluble in the vial or pen but possibly insoluble in the depot). Although not wishing to be constrained by theory, the zinc-free monomers and dimers could provide the prandial component; the zinc-stabilized hexamer aggregates would provide the long-acting component. Also not wishing to be constrained by theory, it is a further possibility that single-chain insulin analogues, when present as monomeric protein molecules in the blood stream, may exhibit biphasic signaling properties at target cells through intrinsic features of their hormone-receptor signaling complexes, such that their pharmacodynamics properties may in this way mimic the biphasic pharmacokinetic properties of existing regular-NPH pre-mixed products.

It is a feature of the present invention that the isoelectric point of the single-chain analogue is between 6.8 and 7.8 such that a soluble formulation is feasible under neutral conditions (pH 7.0-8.0) either in the presence of 2-3 zinc ions per six protein monomers or in the presence of less than 2 zinc ions per six protein monomers such that hexamer assembly would be incomplete. It is thus a feature of the present invention that the single-chain insulin analogue retain a competence to undergo zinc-ion-dependent formation of protein hexamers analogous to the classical zinc insulin hexamer known in the art as $T_6$ insulin hexamer, $T_3R^f_3$ insulin hexamer, or $R_6$ insulin hexamer.

It is also envisioned that single-chain analogues may also be made with A- and B-domain sequences derived from animal insulins, such as porcine, bovine, equine, and canine insulins, by way of non-limiting examples. In addition or in the alternative, the insulin analogue of the present invention may contain a deletion of residues B1-B3 or may be combined with a variant B chain lacking Lysine (e.g., LysB29 in wild-type human insulin) to avoid Lys-directed proteolysis of a precursor polypeptide in yeast biosynthesis in *Pichia pastoris*, *Saccharomyces cerevisciae*, or other yeast expression species or strains. The B-domain of the single-chain insulin of the present invention may optionally contain non-standard substitutions, such as D-amino-acids at positions B20 and/or B23 (intended to augment thermodynamic stability, receptor-binding affinity, and resistance to fibrillation), a halogen modification at the 2 ring position of $Phe^{B24}$ (i.e., ortho-F-$Phe^{B24}$, ortho-Cl-$Phe^{B24}$, or ortho-Br-$Phe^{B24}$; intended to enhance thermodynamic stability and resistance to fibrillation), 2-methyl ring modification of $Phe^{B24}$ (intended to enhance receptor-binding affinity), and/or introduction of iodo-substitutions within the aromatic ring of $Tyr^{B16}$ and/or $Tyr^{B26}$ (3-mono-iodo-Tyr or [3, 5]-di-iodo- Tyr); intended to augment thermodynamic stability and receptor-binding activity). It is also envisioned that Thr$^{B27}$, Thr$^{B30}$, or one or more Serine residues in the C-domain may be modified, singly or in combination, by a monosaccaride adduct; examples are provided by O-linked N-acetyl-D-galactopyranoside (designated GalNAc-O-Ser or GalNAc-O-Thr), O-linked-D-mannopyranoside (mannose-O-Ser or mannose-O-Thr), and/or -D-glucopyranoside (glucose-O-Ser or glucose-O-Thr).

Furthermore, in view of the similarity between human and animal insulins, and use in the past of animal insulins in human patients with diabetes mellitus, it is also envisioned that other minor modifications in the sequence of insulin may be introduced, especially those substitutions considered "conservative." For example, additional substitutions of amino acids may be made within groups of amino acids with similar side chains, without departing from the present invention. These include the neutral hydrophobic amino acids: Alanine (Ala or A), Valine (Val or V), Leucine (Leu or L), Isoleucine (Ile or I), Proline (Pro or P), Tryptophan (Trp or W), Phenylalanine (Phe or F) and Methionine (Met or M). Likewise, the neutral polar amino acids may be substituted for each other within their group of Glycine (Gly or G), Serine (Ser or S), Threonine (Thr or T), Tyrosine (Tyr or Y), Cysteine (Cys or C), Glutamine (Glu or Q), and Asparagine (Asn or N). Basic amino acids are considered to include Lysine (Lys or K), Arginine (Arg or R) and Histidine (His or H). Acidic amino acids are Aspartic acid (Asp or D) and Glutamic acid (Glu or E). Unless noted otherwise or wherever obvious from the context, the amino acids noted herein should be considered to be L-amino acids. Standard amino acids may also be substituted by non-standard amino acids belong to the same chemical class. By way of non-limiting example, the basic side chain Lys may be replaced by basic amino acids of shorter side-chain length (Ornithine, Diaminobutyric acid, or Diaminopropionic acid). Lys may also be replaced by the neutral aliphatic isostere Norleucine (Nle), which may in turn be substituted by analogues containing shorter aliphatic side chains (Aminobutyric acid or Aminopropionic acid).

The amino-acid sequence of human proinsulin is provided, for comparative purposes, as SEQ ID NO: 1.

The amino-acid sequence of the B chain of human insulin is provided as SEQ ID NO: 3.

```
(human B chain)
                                               SEQ ID NO: 3
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Thr
```

The amino-acid sequence of the modified B chain of KP-insulin (insulin lispro, the active component of Humalog®; Eli Lilly and Co.) is provided as SEQ ID NO: 4.

```
(human "KP" B chain)
                                               SEQ ID NO: 4
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Lys-Pro-Thr
```

Figure 1:
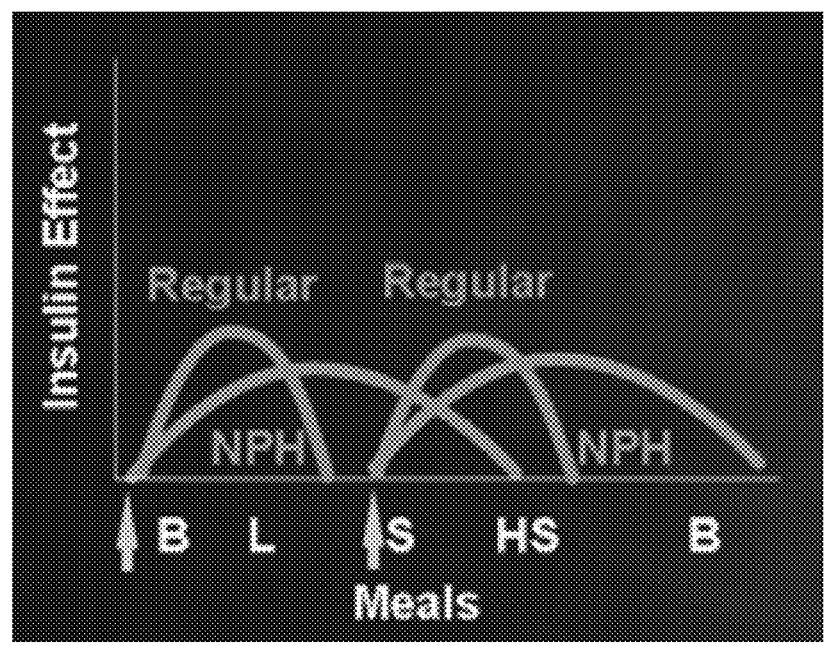
FIG. 1. Schematic goal of biphasic insulin products. Original implementation used wild-type insulin (regular and NPH) whereas current products employ prandial insulin analogs. This figure was obtained from R. Beaser & S. Braunstein, MedScape Multispeciality (Education/CME section; 2009) (www.medscape.org/viewarticle/708784).
Figure 2:
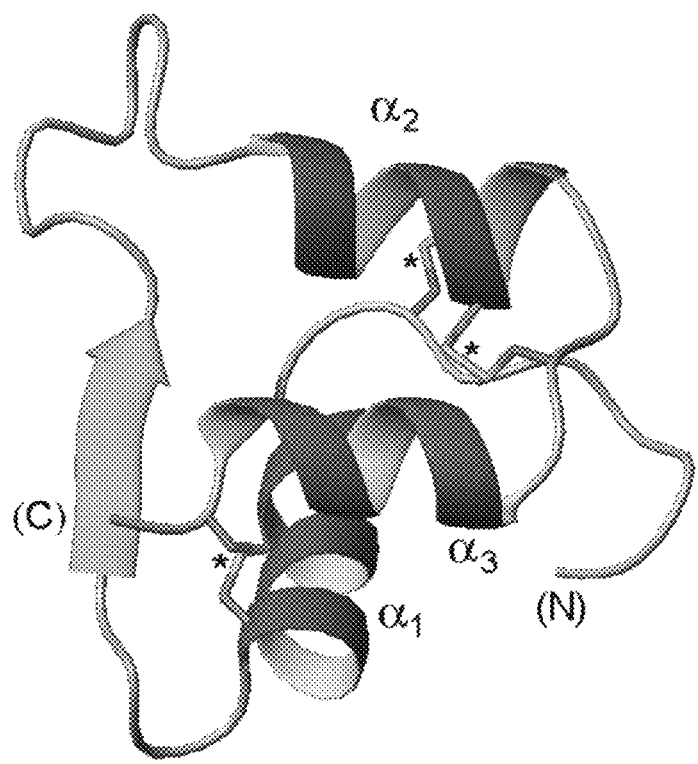
FIG. 2. Ribbon model of 57-residue SCI. —Helices are shown in red (outside) and yellow (inside), and the B24-B28-strand in blue (arrow). The three disulfide bridges (cystines) are shown (asterisks). The C-domain (Sequence GGGPRR) is well ordered (Hua, Q. X., et al. *J. Biol. Chem.* 283, 14703-16 (2008)).
Figure 3:
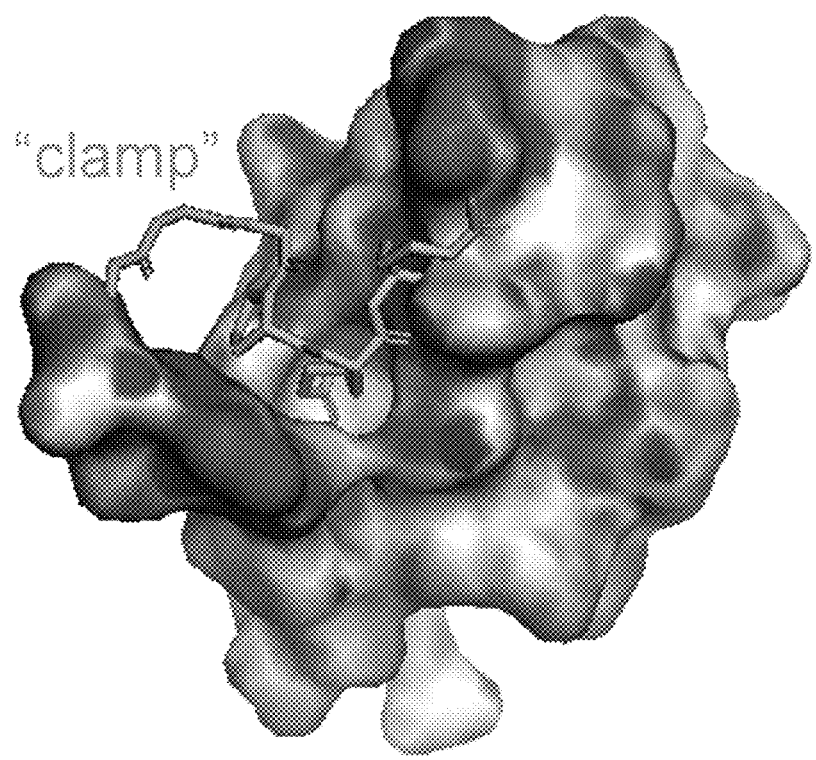
FIG. 3. Molecular structure of the 57-residue SCI platform. The six-residue C-domain (sticks; turquoise) provides a tether between A- and B domains (space-filling representation). The surface is color-coded according to electrostatic potential in standard GRASP format (red, electronegative.

SEQ ID NO 5 provides the amino-acid sequence of a single-chain insulin analogue that has been previously disclosed (Hua, Q. X., et al. J. Biol. Chem. 283, 14703-16 (2008)) and whose structure is shown in FIGS. 1 and 2. Unlike the analogues of the present invention, this sequence lacks acid residues at positions A14, C1 and C2 and contains an acidic residue at position B10; the resulting single-chain insulin analogue does not exhibit the desired biphasic pharmacodynamics properties of the present invention.

The amino-acid sequence of single-chain insulin analogues of the present invention are in part given in SEQ ID NO 6-19, corresponding to single-chain insulin analogs. These sequences employ standard single-letter code, such that Ala is represented by A, Cysteine is represented by C, Aspartic Acid is represented by D, Glutamic Acid is represented by E, and so forth as is known in the art. Elements in red indicate sequences or substitutions not present in wild-type insulin or wild-type proinsulin. Dashes in SEQ ID NO 13 and 19 indicate deletion of N-terminal residues B1-B3 (designated des-B1-B3 analogues).

```
(human proinsulin)
                                               SEQ ID NO: 1
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Thr-Arg-Arg-Glu-Ala-Glu-Asp- Leu-Gln-Val-Gly-Gln-Val-Glu-Leu-Gly-Gly-Gly-Pro- Gly-Ala-Gly-Ser-Leu-Gln-Pro-Leu-Ala-Leu-Glu-Gly- Ser-Leu-Gln-Lys-Arg-Gly-Ile-Val-Glu-Gln-Cys-Cys- Thr-Ser-Ile-Cys-Ser-Leu-Tyr-Gln-Leu-Glu-Asn-Tyr- Cys-Asn
```

The amino-acid sequence of the A chain of human insulin is provided as SEQ ID NO: 2.

```
(human A chain)
                                               SEQ ID NO: 2
Gly-Ile-Val-Glu-Gln-Cys-Cys-Thr-Ser-Ile-Cys-Ser- Leu-Tyr-Gln-Leu-Glu-Asn-Tyr-Cys-Asn
```

```
                                               SEQ ID NO: 5
F V N Q H L C G S D L V E A L Y L V C G E R G F F

Y T D P T G G G P R R G I V E Q C C H S I C S L Y

Q L E N Y C N

SEQ ID NO: 6
F V N Q H L C G S H L V E A L Y L V C G E R G F F

Y T D P T G G G P R R G I V E Q C C H S I C S L E

Q L E N Y C N

SEQ ID NO: 7
F V N Q H L C G S H L V E A L Y L V C G E R G F F

Y T D P T G E G P R R G I V E Q C C H S I C S L E

Q L E N Y C N

SEQ ID NO: 8
F V N Q H L C G S H L V E A L Y L V C G E R G F F

Y T D P T E E G P R R G I V E Q C C H S I C S L E

Q L E N Y C N
```

SEQ ID NO: 9
F V N Q H L C G S H L V E A L Y L V C G E R G F F
Y T D P T E E G P R R G I V E Q C C H S I C S W E
Q L E N Y C N

SEQ ID NO: 10
F V N Q H L C G S H L V E A L Y L V C G E R G F F
Y T P E T E E G P R R G I V E Q C C H S I C S L E
Q L E N Y C N

SEQ ID NO: 11
F V N Q H L C G S H L V E A L Y L V C G E R G F F
Y T P R T E E G P R R G I V E Q C C H S I C S L E
Q L E N Y C N

SEQ ID NO: 12
F V N Q H L C G S H L V E A L Y L V C G E R G F F
Y T E P T E E G P R R G I V E Q C C H S I C S L E
Q L E N Y C N (des-B1-B3)
SEQ ID NO: 13
- - - Q H L C G S H L V E A L Y L V C G E R G F F Y
T P E T E E G P R R G I V E Q C C H S I C S L E
Q L E N Y C N SEQ ID NO: 14
F V N Q H L C G S H L V E A L Y L V C G E R G F
F Y T D P T E E G P R R G I V E Q C C H S I C S
L E Q L E N Y C N SEQ ID NO: 15
F V N Q H L C G S H L V E A L Y L V C G E R G F
F Y T D P T E E G R R G I V E Q C C H S I C S L
E Q L E N Y C N SEQ ID NO: 16
F V N Q H L C G S H L V E A L Y L V C G E R G F
F Y T D P T E E R R G I V E Q C C H S I C S L E
Q L E N Y C N SEQ ID NO: 17
F V N Q H L C G S H L V E A L Y L V C G E R G F
F Y T D P T E E R G I V E Q C C H S I C S L E Q
L E N Y C N SEQ ID NO: 18
F V N Q H L C G S H L V Q A L Y L V C G E R G F
F Y T P E T E E G P R R G I V E Q C C H S I C S
L E Q L E N Y C N (des-B1-B3)
SEQ ID NO: 19
- - - Q H L C G S H L V E A L Y L V C G E R G F F Y
T D P T E E G P R R G I V E Q C C H S I C S L E
Q L E N Y C N Amino-acids sequence of single-chain insulin analogues of the present invention are also given in SEQ ID NO 20-34, corresponding to single-chain insulin analogs with optional elements at positions indicated by $X_1$, $X_2$, and so forth; these positions are indicated in green. As above, elements in red indicate sequences or substitutions that are otherwise not present in wild-type insulin or wild-type proinsulin. Dashes in SEQ ID NO 13 and 19 indicate deletion of N-terminal residues B1-B3 (designated des-B1-B3 analogues).

SEQ ID NO: 20
F V N Q H L C G S H L V E A L Y L V C G E R G F F
Y T $X_1$ P T E S P R R G I V E Q C C $X_2$ S I
C S L $X_3$ Q L E N Y C N

SEQ ID NO: 21
F V N Q H L C G S H L V E A L Y L V C G E R G F
F Y T $X_1$ P T S E G P R R G I V E Q C C $X_2$ S
I C S L $X_3$ Q L E N Y C N

SEQ ID NO: 22
F V N Q H L C G S H L V E A L Y L V C G E R G F
F Y T $X_1$ P T G E G P R R G I V E Q C C $X_2$ S I
C S L $X_3$ Q L E N Y C N

SEQ ID NO: 23
F V N Q H L C G S H L V E A L Y L V C G E R G F
F Y T $X_1$ P T E E G P R R G I V E Q C C $X_2$ S I C
S L $X_3$ Q L E N Y C N

SEQ ID NO: 24
F V N Q H L C G S H L V E A L Y L V C G E R G F
F Y T $X_1$ P T E E G P R R G I V E Q C C $X_2$ S I C
S $X_4$ $X_3$ Q L E N Y C N

SEQ ID NO: 25
F V N Q H L C G S H L V E A L Y L V C G E R G F
F Y T P $X_4$ T E E G P R R G I V E Q C C $X_2$ S I C
S L $X_3$ Q L E N Y C N

SEQ ID NO: 26
F V N Q H L C G S H L V E A L Y L V C G E R G F
F Y T P $X_4$ T E E G P R R G I V E Q C C $X_2$ S I C
S L $X_3$ Q L E N Y C N

SEQ ID NO: 27
F V N Q H L C G S H L V E A L Y L V C G E R G F
F Y T $X_4$ P T E E G P R R G I V E Q C C $X_2$ S I C
S L $X_3$ Q L E N Y C N (des-B1-B3)
SEQ ID NO: 28
- - - Q H L C G S H L V E A L Y L V C G E R G F F
Y T P $X_4$ T E E G P R R G I V E Q C C $X_2$ S I C
S L $X_3$ Q L E N Y C N SEQ ID NO: 29
F V N Q H L C G S H L V E A L Y L V C G E R G
F F Y T $X_1$ P T E E G P R R G I V E Q C C $X_2$ S
I C S L $X_3$ Q L E N Y C N SEQ ID NO: 30
F V N Q H L C G S H L V E A L Y L V C G E R G
F F Y T X₁ P T E E G R R G I V E Q C C X₂ S I
C S L X₃ Q L E N Y C N SEQ ID NO: 31
F V N Q H L C G S H L V E A L Y L V C G E R G
F F Y T X₁ P T E E R R G I V E Q C C X₂ S I C
S L X₃ Q L E N Y C N SEQ ID NO: 32
F V N Q H L C G S H L V E A L Y L V C G E R G
F F Y T X₁ P T E E R G I V E Q C C X₂ S I C S
L X₃ Q L E N Y C N SEQ ID NO: 33
F V N Q H L C G S H L V Q A L Y L V C G E R G
F F Y T P X₄ T E E G P R R G I V E Q C C X₂ S
I C S L X₃ Q L E N Y C N (des-B1-B3)
SEQ ID NO: 34
- - - Q H L C G S H L V E A L Y L V C G E R G F
F Y T X₁ P T E E G P R R G I V E Q C C X₂ S
I C S L X₃ Q L E N Y C N Where X₁ is chosen from the group Ala, Arg, Asn, Asp, Gln, Glu, or Lys; X₂ is chosen from the group Ala, Arg, Gln, Glu, or Lys; X₃ is chosen from the group Gln, Glu, Phe, Trp, or Tyr; and X₁ is chosen from the group Ala, Arg, Glu, Lys, or Pro.

Amino-acids sequence of single-chain insulin analogues of the present invention are also given in SEQ ID NO 35-49, corresponding to single-chain insulin analogs with optional elements at positions in the connecting domain as indicated by Y₁, Y₂, and so forth (magenta) and as including the above optional sequence features X₁, X₂, and so forth as indicated in green. As above, elements in red indicate sequences or substitutions that are otherwise not present in wild-type insulin or wild-type proinsulin. Dashes in SEQ ID NO 13 and 19 indicate deletion of N-terminal residues B1-B3 (designated des-B1-B3 analogues).

SEQ ID NO: 35
F V N Q H L C G S H L V E A L Y L V C G E R G F F
Y T X₁ P T Y₁ S G P R R G I V E Q C C X₂ S I C S L
X₃ Q L E N Y C N

SEQ ID NO: 36
F V N Q H L C G S H L V E A L Y L V C G E R G F F
Y T X₁ P T S Y₂ G P R R G I V E Q C C X₂ S I C S L
X₃ Q L E N Y C N

SEQ ID NO: 37
F V N Q H L C G S H L V E A L Y L V C G E R G F F
Y T X₁ P T Y₁ E G P R R G I V E Q C C X₂ S I C S L
X₃ Q L E N Y C N

SEQ ID NO: 38
F V N Q H L C G S H L V E A L Y L V C G E R G F F
Y T X₁ P T Y₁ Y₂ G P R R G I V E Q C C X₂ S I C S
L X₃ Q L E N Y C N

SEQ ID NO: 39
F V N Q H L C G S H L V E A L Y L V C G E R G F F
Y T X₁ P T Y₁ Y₂ G P R R G I V E Q C C X₂ S I C S
X₄ X₃ Q L EN Y C N

SEQ ID NO: 40
F V N Q H L C G S H L V E A L Y L V C G E R G F F
Y T P X₁ T Y₁ Y₂ G P R R G I V E Q C C X₂ S I C S
L X₃ Q L E N Y C N

SEQ ID NO: 41
F V N Q H L C G S H L V E A L Y L V C G E R G F F
Y T P X₁ T Y₁ Y₂ G P R R G I V E Q C C X₂ S I C S
L X₃ Q L E N Y C N

SEQ ID NO: 42
F V N Q H L C G S H L V E A L Y L V C G E R G F F
Y T X₁ P T Y₁ Y₂ G P R R G I V E Q C C X₂ S I C S
L X₃ Q L E N Y C N (des-B1-B3)
SEQ ID NO: 43
- - - Q H L C G S H L V E A L Y L V C G E R G F F Y
T P X₁ T Y₁ Y₂ G P R R G I V E Q C C X₂ S I C S L
X₃ Q L E N Y C N SEQ ID NO: 44
F V N Q H L C G S H L V E A L Y L V C G E R G F F
Y T X₁ P T Y₁ Y₂ G P R R G I V E Q C C X₂ S I C S
L X₃ Q L E N Y C N SEQ ID NO: 45
F V N Q H L C G S H L V E A L Y L V C G E R G F F
Y T X₁ P T Y₁ Y₂ G R R G I V E Q C C X₂ S I C S L
X₃ Q L E N Y C N SEQ ID NO: 46
F V N Q H L C G S H L V E A L Y L V C G E R G F F
Y T X₁ P T Y₁ Y₂ R R G I V E Q C C X₂ S I C S L
X₃ Q L E N Y C N SEQ ID NO: 47
F V N Q H L C G S H L V E A L Y L V C G E R G F F
Y T X₁ P T Y₁ Y₂ R G I V E Q C C X₂ S I C S L X₃
Q L E N Y C N SEQ ID NO: 48
F V N Q H L C G S H L V Q A L Y L V C G E R G F F
Y T P X₁ T Y₁ Y₂ G P R R G I V E Q C C X₂ S I C S
L X₃ Q L E N Y C N (des-B1-B3)

SEQ ID NO: 49
- - - Q H L C G S H L V E A L Y L V C G E R G F F Y

T X$_1$ P T Y$_1$ Y$_2$ G P R R G I V E Q C C X$_2$ S I C S L

X$_3$ Q L E N Y C N

Where X$_1$ is chosen from the group Ala, Arg, Asn, Asp, Gln, Glu, or Lys; X$_2$ is chosen from the group Ala, Arg, Gln, Glu, or Lys; X$_3$ is chosen from the group Gln, Glu, Phe, Trp, or Tyr; X$_1$ is chosen from the group Ala, Arg, Glu, Lys, or Pro; and where Y$_1$ and Y$_2$ are each either Asp or Glu.

Amino-acids sequence of single-chain insulin analogues of the present invention are also given in SEQ ID NO 50-64, corresponding to single-chain insulin analogs with additional 1-5 amino-acid residues (designated B$_{1-5}$ in blue below), with optional elements at positions in the connecting domain as indicated by Y$_1$, Y$_2$, and so forth (magenta) and as including the above optional sequence features X$_1$, X$_2$, and so forth as indicated in green. As above, elements in red indicate sequences or substitutions that are otherwise not present in wild-type insulin or wild-type proinsulin. Dashes in SEQ ID NO 13 and 19 indicate deletion of N-terminal residues B1-B3 (designated des-B1-B3 analogues).

SEQ ID NO: 50
F V N Q H L C G S H L V E A L Y L V C G E R G F F

Y T X$_1$ P T Y$_1$ S G P B$_{1-5}$ R R G I V E Q C C X$_2$ S I

C S L X$_3$ Q L E N Y C N

SEQ ID NO: 51
F V N Q H L C G S H L V E A L Y L V C G E R G F F

Y T X$_1$ P T S Y$_2$ G P B$_{1-5}$ R R G I V E Q C C X$_2$ S I

C S L X$_3$ Q L E N Y C N

SEQ ID NO: 52
F V N Q H L C G S H L V E A L Y L V C G E R G F F

Y T X$_1$ P T Y$_1$ E G P B$_{1-5}$ R R G I V E Q C C X$_2$ S I

C S L X$_3$ Q L E N Y C N

SEQ ID NO: 53
F V N Q H L C G S H L V E A L Y L V C G E R G F F

Y T X$_1$ P T Y$_1$ Y$_2$ G P B$_{1-5}$ R R G I V E Q C C X$_2$ S I

C S L X$_3$ Q L E N Y C N

SEQ ID NO: 54
F V N Q H L C G S H L V E A L Y L V C G E R G F F

Y T X$_1$ P T Y$_1$ Y$_2$ G P B$_{1-5}$ R R G I V E Q C C X$_2$ S I

C S X$_4$ X$_3$ Q L E N Y C N

SEQ ID NO: 55
F V N Q H L C G S H L V E A L Y L V C G E R G F F

Y T P X$_1$ T Y$_1$ Y$_2$ G P B$_{1-5}$ R R G I V E Q C C X$_2$ S I

C S L X$_3$ Q L E N Y C N

SEQ ID NO: 56
F V N Q H L C G S H L V E A L Y L V C G E R G F F

Y T P X$_1$ T Y$_1$ Y$_2$ G P B$_{1-5}$ R R G I V E Q C C X$_2$ S I

C S L X$_3$ Q L E N Y C N

SEQ ID NO: 57
F V N Q H L C G S H L V E A L Y L V C G E R G F F

Y T X$_1$ P T Y$_1$ Y$_2$ G P B$_{1-5}$ R R G I V E Q C C X$_2$ S I

C S L X$_3$ Q L E N Y C N (des-B1-B3)

SEQ ID NO: 58
- - - Q H L C G S H L V E A L Y L V C G E R G F F Y T

P X$_1$ T Y$_1$ Y$_2$ G P B$_{1-5}$ R R G I V E Q C C X$_2$ S I C S

L X$_3$ Q L E N Y C N

SEQ ID NO: 59
F V N Q H L C G S H L V E A L Y L V C G E R G F F

Y T X$_1$ P T Y$_1$ Y$_2$ G P B$_{1-5}$ R R G I V E Q C C X$_2$ S I

C S L X$_3$ Q L E N Y C N

SEQ ID NO: 60
F V N Q H L C G S H L V E A L Y L V C G E R G F F

Y T X$_1$ P T Y$_1$ Y$_2$ G B$_{1-5}$ R R G I V E Q C C X$_2$ S I C

S L X$_3$ Q L E N Y C N

SEQ ID NO: 61
F V N Q H L C G S H L V E A L Y L V C G E R G F F

Y T X$_1$ P T Y$_1$ Y$_2$ B$_{1-5}$ R R G I V E Q C C X$_2$ S I C S

L X$_3$ Q L E N Y C N

SEQ ID NO: 62
F V N Q H L C G S H L V E A L Y L V C G E R G F F

Y T X$_1$ P T Y$_1$ Y$_2$ B$_{1-5}$ R G I V E Q C C X$_2$ S I C S L

X$_3$ Q L E N Y C N

SEQ ID NO: 63
F V N Q H L C G S H L V Q A L Y L V C G E R G F F

Y T P X$_1$ T Y$_1$ Y$_2$ G P B$_{1-5}$ R R G I V E Q C C X$_2$ S I

C S L X$_3$ Q L E N Y C N (des-B1-B3)

SEQ ID NO: 64
- - - Q H L C G S H L V E A L Y L V C G E R G F F Y T

X$_1$ P T Y$_1$ Y$_2$ G P B$_{1-5}$ R R G I V E Q C C X$_2$ S I C S

L X$_3$ Q L E N Y C N

Where X$_1$ is chosen from the group Ala, Arg, Asn, Asp, Gln, Glu, or Lys; X$_2$ is chosen from the group Ala, Arg, Gln, Glu, or Lys; X$_3$ is chosen from the group Gln, Glu, Phe, Trp, or Tyr; X$_1$ is chosen from the group Ala, Arg, Glu, Lys, or Pro; where Y$_1$ and Y$_2$ are each either Asp or Glu; and where residues B$_1$, B$_2$, B$_3$, B$_4$, B$_5$, are each optionally present and may be drawn from the group Ala, Asn, Gln, Gly, Pro, Ser or Thr.

The following DNA sequence encodes single-chain insulin analogue specified in SEQ ID NO 6 (see above) with codons optimized for usage patterns in *Pichia pastoris*.

SEQ. ID. NO 65
TTCGTCAATCAACACTTGTGTGGTTCCCACTTGGTTGAGGCATTGTACTT

GGTCTGTGGTGAGAGAGGATTCTTCTACACCGATCCAACTGGTGGTGGTC

The following DNA sequence encodes single-chain insulin analogue specified in SEQ ID NO 7 (see above) with codons optimized for usage patterns in *Pichia pastoris*.

SEQ. ID. NO 66
TTCGTCAATCAACACTTGTGTGGTTCCCACTTGGTTGAGGCATTGTACTT

GGTCTGTGGTGAGAGAGGATTCTTCTACACCGATCCAACTGGTGAGGGTC

CTAGAAGAGGAATCGTCGAGCAATGTTGCCACTCCATTTGTTCCTTGGAA

CAATTGGAAAACTACTGCAACTAA

The following DNA sequence encodes single-chain insulin analogue specified in SEQ ID NO 8 (see above) with codons optimized for usage patterns in *Pichia pastoris*.

SEQ. ID. NO 67
TTCGTCAATCAGCACTTGTGTGGTTCCCACTTGGTTGAGGCTTTGTACTT

GGTTTGTGGTGAGAGAGGTTTCTTCTACACTGATCCAACTGAAGAGGGTC

CAAGAAGAGGTATCGTTGAGCAGTGTTGTCACTCCATCTGTTCCTTGGAG

CAGTTGGAGAACTACTGTAACTGA

The following DNA sequence encodes single-chain insulin analogue specified in SEQ ID NO 9 (see above) with codons optimized for usage patterns in *Pichia pastoris*.

SEQ. ID. NO 68
TTCGTCAATCAGCACTTGTGTGGTTCCCACTTGGTTGAGGCTTTGTACTT

GGTTTGTGGTGAGAGAGGTTTCTTCTACACTGATCCAACTGAAGAGGGTC

CAAGAAGAGGTATCGTTGAGCAGTGTTGTCACTCCATCTGTTCCTGGGAG

CAGTTGGAGAACTACTGTAACTGA

The following DNA sequence encodes single-chain insulin analogue specified in SEQ ID NO 10 (see above) with codons optimized for usage patterns in *Pichia pastoris*.

SEQ. ID. NO 69
TTCGTCAATCAGCACTTGTGTGGTTCCCACTTGGTTGAGGCTTTGTACTT

GGTTTGTGGTGAGAGAGGTTTCTTCTACACTCCAGAAACTGAAGAGGGTC

CAAGAAGAGGTATCGTTGAGCAGTGTTGTCACTCCATCTGTTCCTTGGAG

CAGTTGGAGAACTACTGTAACTGA

The following DNA sequence encodes single-chain insulin analogue specified in SEQ ID NO 11 (see above) with codons optimized for usage patterns in *Pichia pastoris*.

SEQ. ID. NO 70
TTCGTCAATCAGCACTTGTGTGGTTCCCACTTGGTTGAGGCTTTGTACTT

GGTTTGTGGTGAGAGAGGTTTCTTCTACACTCCAAGAACTGAAGAGGGTC

CAAGAAGAGGTATCGTTGAGCAGTGTTGTCACTCCATCTGTTCCTTGGAG

CAGTTGGAGAACTACTGTAACTGA

The following DNA sequence encodes single-chain insulin analogue specified in SEQ ID NO 12 (see above) with codons optimized for usage patterns in *Pichia pastoris*.

SEQ. ID. NO 71
TTCGTCAATCAGCACTTGTGTGGTTCCCACTTGGTTGAGGCTTTGTACTT

GGTTTGTGGTGAGAGAGGTTTCTTCTACACTGAGCCAACTGAAGAGGGTC

CAAGAAGAGGTATCGTTGAGCAGTGTTGTCACTCCATCTGTTCCTTGGAG

CAGTTGGAGAACTACTGTAACTGA

The following DNA sequence encodes single-chain insulin analogue specified in SEQ ID NO 13 (see above) with codons optimized for usage patterns in *Pichia pastoris*.

SEQ. ID. NO 72
TTCGTCAAACAGCACTTGTGTGGTTCCCACTTGGTTGAGGCTTTGTACTT

GGTTTGTGGTGAGAGAGGTTTCTTCTACACTCCAGAAACTGAAGAGGGTC

CAAGAAGAGGTATCGTTGAGCAGTGTTGTCACTCCATCTGTTCCTTGGAG

CAGTTGGAGAACTACTGTAACTGA

The following DNA sequence encodes single-chain insulin analogue specified in SEQ ID NO 15 (see above) with codons optimized for usage patterns in *Pichia pastoris*.

SEQ. ID. NO 73
TTCGTTAACCAGCACTTGTGTGGTTCCCACTTGGTTGAGGCTTTGTACTT

GGTTTGTGGTGAGAGAGGTTTCTTCTACACTGATCCAACTGAAGAGAGAA

GAGGTATCGTTGAGCAGTGTTGTCACTCCATCTGTTCCTTGGAGCAGTTG

GAGAACTACTGTAACTAA

The following DNA sequence encodes single-chain insulin analogue specified in SEQ ID NO 16 (see above) with codons optimized for usage patterns in *Pichia pastoris*.

SEQ. ID. NO 74
TTCGTTAACCAGCACTTGTGTGGTTCCCACTTGGTTGAGGCTTTGTACTT

GGTTTGTGGTGAGAGAGGTTTCTTCTACACTGATCCAACTGAAGAGAGAA

GAGGTATCGTTGAGCAGTGTTGTCACTCCATCTGTTCCTTGGAGCAGTTG

GAGAACTACTGTAACTAA

The following DNA sequence encodes single-chain insulin analogue specified in SEQ ID NO 17 (see above) with codons optimized for usage patterns in *Pichia pastoris*.

SEQ. ID. NO 75
TTCGTTAACCAGCACTTGTGTGGTTCCCACTTGGTTGAGGCTTTGTACTT

GGTTTGTGGTGAGAGAGGTTTCTTCTACACTGATCCAACTGAAGAGAGAG

GTATCGTTGAGCAGTGTTGTCACTCCATCTGTTCCTTGGAGCAGTTGGAG

AACTACTGTAACTAA

The following DNA sequence encodes single-chain insulin analogue specified in SEQ ID NO 18 (see above) with codons optimized for usage patterns in *Pichia pastoris*.

SEQ. ID. NO 76
TTCGTCAATCAGCACTTGTGTGGTTCCCACTTGGTTCAGGCTTTGTACTT

GGTTTGTGGTGAGAGAGGTTTCTTCTACACTCCAGAAACTGAAGAGGGTC

-continued

CAAGAAGAGGTATCGTTGAGCAGTGTTGTCACTCCATCTGTTCCTTGGAG

CAGTTGGAGAACTACTGTAACTGA

The following DNA sequence encodes single-chain insulin analogue specified in SEQ ID NO 19 (see above) with codons optimized for usage patterns in Pichia pastoris.

SEQ. ID. NO 77
TTCGTCAAACAGCACTTGTGTGGTTCCCACTTGGTTGAGGCTTTGTACTT

GGTTTGTGGTGAGAGAGGTTTCTTCTACACTGACCCAACTGAAGAGGGTC

CAAGAAGAGGTATCGTTGAGCAGTGTTGTCACTCCATCTGTTCCTTGGAG

CAGTTGGAGAACTACTGTAACTGA

Analogous synthetic genes have been prepared and cloned in Pichia pastoris encoding SCI-59A (see below) and derivatives of SCI-59A and SCI-59B containing the additional substitution Glu$^{B13}$→Gln as embodied in SEQ. ID NO 31-37.

Two single-chain insulin analogues of the present invention (encoded by SEQ ID NO 8 and SEQ ID NO 10; respectively designated SCI-57DP and SCI-57PE) were prepared by biosynthesis of a precursor polypeptide in Pichia pastoris; this system secretes a folded protein containing native disulfide bridges with cleavage N-terminal extension peptide. Efficiency of over-expression (>200 mg/l culture in fermentation) is illustrated in FIG. 5. The cleaved single-chain insulin products had length 57, the sum of a 30-residue B-domain, 6-residue C-domain (sequence EEG-PRR in each case), and 21-residue A-domain. The formal isoelectric points (pI) of SCI-57DP and SCI-57PE were in each case predicted to be shifted below 5.0 by the removal of a positive charge at wild-type position B29 (LysB29), by acidic substitutions at B28 or B29, by an acidic substitution at A14 (TyrA14→Glu), and by offsetting basic and acidic side chains in the C-domain.

The thermodynamic stabilities of the single-chain analogues were probed by CD-monitored guanidine denaturation as described (Hua, Q. X., et al. J. Biol. Chem. 283, 14703-16 (2008)). The results (column 2 of Table 1) indicate that SCI-57DP and SCI-57PE are each more stable to chemical denaturation than are wild-type insulin or KP-insulin. In each case higher concentrations of guanidine-HCl were required to achieve 50% unfolding of the protein (column 3 in Table 1); a trend is observed toward larger values of m (column 4), suggesting more efficient desolvation of nonpolar surfaces in the folded state. The susceptibility of SCI-57PE to fibrillation on gentle agitation at 37° C. was found to be markedly prolonged relative to wild-type insulin or KP-insulin (column 5 of Table 1). Whereas wild-type insulin and KP-insulin form fibrils in less than 10 days under these conditions, SCI-57PE is refractory to fibrillation for at least 9 months.

The receptor-binding affinities of SCI-57DP and SCI-57PE were determined in relation to wild-type human insulin. The assay employed the A isoform of the insulin receptor. Relative to human insulin (equilibrium dissociation constant 0.05(±0.01) nM), SCI-57DP and SCI-57PE exhibited respective binding constants of 0.06(±0.01) nM and 0.08(±0.01) nM. The affinity of SCI-57DP for the mitogenic Type 1 IGF-I receptor was at least fivefold lower than that of wild-type human insulin. The protocol for assay of receptor-binding activities was as follows. Microtiter strip plates (Nunc Maxisorb) were incubated overnight at 4° C. with AU5 IgG (100 μl/well of 40 mg/ml in phosphate-buffered saline). Binding data were analyzed by a two-site sequential model. Data were corrected for nonspecific binding (amount of radioactivity remaining membrane associated in the presence of 1 M human insulin. In all assays the percentage of tracer bound in the absence of competing ligand was less than 15% to avoid ligand-depletion artifacts. Dissociation constants (IQ were determined by fitting to a mathematic model as described by Whittaker and Whittaker (2005. J. Biol. Chem. 280: 20932-20936); the model employed non-linear regression with the assumption of heterologous competition (Wang, 1995, FEBS Lett. 360: 111-114).

TABLE 1

Thermodynamic and Physical Stabilities
Insulin Analogues at 25° C.$^a$

| analog | $\Delta G_u^b$ kcal/mol | $C_{mid}$ (M)$^c$ | m (kcal/mol/M)$^d$ | fib. lag time$^e$ |
|---|---|---|---|---|
| WT insulin | 3.6 ± 0.1 | 4.9 ± 0.07 | 0.73 ± 0.01 | 3-6 days |
| KP-insulin | 3.1 ± 0.1 | 4.5 ± 0.1 | 0.69 ± 0.01 | 2-4 days |
| SCI-57DP | 4.3 ± 0.1 | 5.7 ± 0.13 | 0.74 ± 0.02 | ND$^f$ |
| SCI-57PE | 4.6 ± 0.1 | 5.7 ± 0.11 | 0.80 ± 0.02 | >9 mo |

$^a$Thermodynamic stabilities were inferred from CD-detected guanidine denaturation (222 nm) at 25° C. analyzed by a two-state model extrapolated to zero denaturant concentration.
$^b\Delta G_u$ represents the apparent change in free energy on denaturation in guanidine-HCl as extrapolated to zero denaturant concentration by a two-state model.
$^cC_{mid}$ is defined as that concentration of guanidine-HCl at which 50% of the protein is unfolded.
$^d$ The m value is the slope of unfolding free energy $\Delta G_u$ versus molar concentration of denaturant; it correlates with the extent of exposure of nonpolar surfaces on denaturation.
$^e$Fibrillation lag time was measure in days prior to onset of thioflavin-T-positive aggregation; analogues in triplicate were gently rocked at 45° C. in Tris-HCl formulation at a nominal strength of U-100.
$^f$ND; not determined Biological activity and pharmacodynamics were tested in male Sprague-Dawley rats (ca. 300 g) rendered diabetic by streptozotocin (FIG. 6). PD effects of s.q. injection of U-100 (0.6 mM) SCI-57PE and SCI-57DP were evaluated in relation to Humalog® and the 25-75 Humalog® pre-mix; the resulting overall profile of the blood-glucose concentration (FIG. 6A) indicated that the PD properties of our two candidates are similar to the pre-mixed Lilly product, recapitulating both its long-acting (120-540 min) and rapid-acting components (FIG. 6B). Initial rates of decline of the blood glucose concentration over the first hour post-injection are shown in FIG. 7.

Thermal Stability of SCIs.

Retention or loss of potency of SCI-57DP was evaluated in the above rats under conditions favoring rapid degradation of current insulin products (i.e., gentle agitation at 45° C. in a glass vial in the presence of an air-liquid interface; FIG. 8). Fresh materials were employed in FIG. 8A. Controls were provided by Humalog® and Lantus®. Whereas Lantus® was inactive after 11 days (○ in FIG. 8B) and Humalog® within 5 days (not shown), SCI-2 (♦ and □) maintained full activity when tested as a clear solution after 57 days (FIG. 8B). SCI-57PE (whose $G_u$ is greater than that of SCI-DP; Table 1 above), exhibits similar resistance to degradation (not shown).

Structural studies employed circular dichroism (CD) and NMR spectroscopy. The far-ultraviolet CD spectra of SCI-57DP and SCI-57PE indicated a predominance of alpha-helix in accordance with the native structure of human insulin and with the solution structure of a single-chain insulin analogue (Hua, Q. X., et al. J. Biol. Chem. 283, 14703-16 (2008)). The NMR studies focused on SCI-57DP in aqueous solution (pH 7-8) in the absence of zinc ions in light of its monomeric status at protein concentrations <1 mM. Spectra were acquired at a proton frequency of 700 MHz. The 2D-NMR NOESY spectrum and $^{1}$H—$^{15}$N heteronuclear single-quantum coherence (HSQC) 2D "fingerprint" spectrum provided evidence for a folded structure; patterns of NOEs and chemical shifts are in accord with prior analysis of a 57-residue single-chain insulin analogue (Hua, Q. X., et al. *J. Biol. Chem.* 283, 14703-16 (2008)).

Speed of hexamer disassembly was evaluated in $R_6$ cobalt hexamers of SCI-1 at 25° C. and pH 7.4 by visible absorption spectroscopy. This assay exploits the blue d-d absorption band of the two tetrahedral $Co^{2+}$ sites in the $R_6$ insulin hexamer to monitor the rate of metal-ion release and sequestration by excess chelator EDTA; the octahedral $Co^{2+}$-EDTA complex is colorless. Remarkably, whereas the Lilly $Co^{2+}$-EDTA sequestration assay of wild-type insulin leads under these conditions to a mono-exponential loss of absorbance at 574 nm (black line in FIG. 9), SCI-1 exhibits a bi-exponential transition with fast phase (more rapid than insulin lispro; not shown) and a slow phase (slower than wild-type insulin; green line in FIG. 9). Among the portfolio of two-chain insulin analogs tested by the Weiss group at CWRU, such biphasic kinetic behavior in the EDTA assay is unprecedented. This assay correlated with PK studies in animals (and subsequently in humans), these spectroscopic results motivated our overarching hypothesis that the present SCIs would exhibit biphasic PK properties in a subcutaneous depot (as in rats). The molecular mechanism of this biphasic behavior remains to be determined but may involve the phenol-dependent RT transition as found in insulin degludec (a new basal analog from Novo-Nordisk).

A method for treating a patient with diabetes mellitus comprises administering a single-chain insulin analogue as described herein. It is another aspect of the present invention that the single-chain insulin analogues may be prepared either in yeast (*Pichia pastoris*) or subject to total chemical synthesis by native fragment ligation. The synthetic route of preparation is preferred in the case of non-standard modifications, such as D-amino-acid substitutions, halogen substitutions within the aromatic rings of Phe or Tyr, or O-linked modifications of Serine or Threonine by carbohydrates; however, it would be feasible to manufacture a subset of the single-chain analogues containing non-standard modifications by means of extended genetic-code technology or four-base codon technology (for review, see Hohsaka, T., & Sisido, M., 2012). It is yet another aspect of the present invention that use of non-standard amino-acid substitutions can augment the resistance of the single-chain insulin analogue to chemical degradation or to physical degradation. We further envision the analogues of the present invention providing a method for the treatment of diabetes mellitus or the metabolic syndrome. The route of delivery of the insulin analogue is by subcutaneous injection through the use of a syringe or pen device.

A single-chain insulin analogue of the present invention may also contain other modifications, such as a halogen atom at positions B24, B25, or B26 as described more fully in co-pending U.S. patent application Ser. No. 13/018,011, the disclosure of which is incorporated by reference herein. An insulin analogue of the present invention may also contain a foreshortened B-chain due to deletion of residues B1-B3 as described more fully in U.S. Provisional Patent Application 61/589,012.

A pharamaceutical composition may comprise such insulin analogues and which may optionally include zinc. Zinc ions may be included at varying zinc ion:protein ratios, ranging from 2.2 zinc atoms per insulin analogue hexamer to 10 zinc atoms per insulin analogue hexamer. The pH of the formulation is in the range pH 7.0-8.0; a buffer (typically sodium phosphate or Tris-hydrochloride) may or may not be present. In such a formulation, the concentration of the insulin analogue would typically be between about 0.6-5.0 mM; concentrations up to 5 mM may be used in vial or pen; the more concentrated formulations (U-200 or higher) may be of particular benefit in patients with marked insulin resistance. Excipients may include glycerol, glycine, arginine, Tris, other buffers and salts, and anti-microbial preservatives such as phenol and meta-cresol; the latter preservatives are known to enhance the stability of the insulin hexamer. Such a pharmaceutical composition may be used to treat a patient having diabetes mellitus or other medical condition by administering a physiologically effective amount of the composition to the patient.

Based upon the foregoing disclosure, it should now be apparent that the single-chain insulin analogues provided will carry out the objects set forth hereinabove. Namely, these insulin analogues exhibit enhanced resistance to fibrillation while retaining desirable pharmacokinetic and pharmacodynamic features (conferring biphasic action) and maintaining at least a fraction of the biological activity of wild-type insulin. It is, therefore, to be understood that any variations evident fall within the scope of the claimed invention and thus, the selection of specific component elements can be determined without departing from the spirit of the invention herein disclosed and described.

The following literature is cited to demonstrate that the testing and assay methods described herein would be understood by one of ordinary skill in the art.

Brange J, editor. (1987) *Galenics of Insulin: The Physicochemical and Pharmaceutical Aspects of Insulin and Insulin Preparations.* Berlin: Springer Berlin Heidelberg.

Hohsaka, T., and Sisido, M. (2012) Incorporation of non-natural amino acids into proteins. *Curr. Opin. Chem. Biol.* 6, 809-15.

Hua, Q. X., Nakagawa, S. H., Jia, W., Huang, K., Phillips, N. B., Hu, S. and Weiss, M. A. (2008) Design of an active ultrastable single-chain insulin analog: synthesis, structure, and therapeutic implications. *J. Biol. Chem.* 283, 14703-14716.

Ilag, L. L., Kerr, L., Malone, J. K., and Tan, M. H. (2007) Prandial premixed insulin analogue regimens versus basal insulin analogue regimens in the management of type 2 diabetes: an evidence-based comparison. *Clin. Ther.* 29, 1254-70.

Jang, H. C., Guler, S., and Shestakova, M. (2008) When glycaemic targets can no longer be achieved with basal insulin in type 2 diabetes, can simple intensification with a modern premixed insulin help? Results from a subanalysis of the PRESENT study. *Int. J. Clin. Pract.* 62, 1013-8.

Kalra, S., Balhara, Y., Sahay, B., Ganapathy, B., and Das, A. (2013) Why is premixed insulin the preferred insulin? Novel answers to a decade-old question. *J. Assoc. Physicians India* 61, 9-11.

Lee, H. C., Kim, S. J., Kim, K. S., Shin, H. C., and Yoon, J. W. (2000) Remission in models of type 1 diabetes by gene therapy using a single-chain insulin analogue. *Nature* 408, 483-8. Retraction in: Lee H C, Kim K S, Shin H C. 2009. *Nature* 458, 600.

Mosenzon, O., and Raz, I. (2013) Intensification of insulin therapy for type 2 diabetic patients in primary care: basal-bolus regimen versus premix insulin analogs: when and for whom? *Diabetes Care* 36 Suppl 2, S212-8.

Phillips, N. B., Whittaker, J., Ismail-Beigi, F., and Weiss, M. A. (2012) Insulin fibrillation and protein design: topological resistance of single-chain analogues to thermal degradation with application to a pump reservoir. *J. Diabetes Sci. Technol.* 6, 277-288.

Qayyum, R., Bolen, S., Maruthur, N., Feldman, L., Wilson, L. M., Marinopoulos, S. S., et al. (2008) Systematic review: comparative effectiveness and safety of premixed insulin analogues in type 2 diabetes. *Ann. Intern. Med.* 149, 549-59.

Rolla, A. R., and Rakel, R. E. (2005) Practical approaches to insulin therapy for type 2 diabetes mellitus with premixed insulin analogues. *Clin. Ther.* 27, 1113-25.

Wang, Z. X. (1995) An exact mathematical expression for describing competitive biding of two different ligands to a protein molecule *FEBS Lett.* 360: 111-114.

Whittaker, J., and Whittaker, L. (2005) Characterization of the functional insulin binding epitopes of the full-length insulin receptor. *J. Biol. Chem.* 280: 20932-20936.

What is claimed is:

1. A single-chain insulin comprising:
   a C-domain of from 6 to 11 amino acid residues comprising at least two acidic residues at the N-terminal side of the C-domain and at least two basic residues at the C-terminal side of the C-domain peptide, wherein the amino acids at the N-terminal side of the C-domain are the amino acids Glu-Glu;
   a basic amino acid residue at the position corresponding to A8 of human insulin, and
   an acidic amino acid residue at the position corresponding to A14 of human insulin.

2. The single-chain insulin of claim 1, wherein the C-domain has the amino acids Arg-Arg, Lys-Lys, Arg-Lys, or Lys-Arg at the C-terminal side of the C-domain.

3. The single-chain insulin of claim 2, wherein the C-domain contains a 2 to 4 amino acid joint region between the acidic residues and the basic residues.

4. The single-chain insulin of claim 3, wherein the joint region comprises one or more of glycine, serine, and proline residues.

5. The single-chain insulin of claim 4, wherein the joint region comprises Gly-Pro.

6. The single-chain insulin of claim 5, wherein the amino acid at the position corresponding to A8 is Lys, Arg, Hist, or Orn.

7. The single-chain insulin of claim 6, wherein the amino acid at the position corresponding to A14 is Glu.

8. The single-chain insulin of claim 7, wherein the single chain insulin comprises an acidic amino acid substitution at the position corresponding to B28 and/or B29.

9. The single-chain insulin of claim 8, having a Histidine at the position corresponding to B10 of human insulin.

10. The single-chain insulin of claim 9, wherein the single chain insulin has a substitution of Gly, Ala, or Ser for Asn at position A21.

11. The single-chain insulin of claim 10, wherein the single chain insulin has the amino acid sequence of any one of SEQ ID NOS: 8-14, 18-19, 23-29, 33-34, 37-44, 48-49 and 52-64.

12. The single-chain insulin of claim 11, wherein the single chain insulin has a predicted isoelectric point below 5.0.

13. A pharmaceutical composition comprising a single-chain insulin formulated at a pH within the range 7.0 to 8.0, wherein the single chain insulin comprises:
- a C-domain of from 6 to 11 amino acid residues comprising at least two acidic residues at the N-terminal side of the C-domain and at least two basic residues at the C-terminal side of the C-domain peptide, wherein the amino acids at the N-terminal side of the C-domain are the amino acids Glu-Glu;
- a basic amino acid residue at the position corresponding to A8 of human insulin, and
- an acidic amino acid residue at the position corresponding to A14 of human insulin.

14. The pharmaceutical composition of claim 13, further comprising a pH buffer.

15. The pharmaceutical composition of claim 14, wherein the single-chain insulin is formulated at a strength of between U-500 and U-1000.

16. The pharmaceutical composition of claim 15, further comprising 2 to 4 zinc ions per insulin hexamer.

17. The pharmaceutical composition of claim 15, further comprising less than 2 zinc ions per insulin hexamer.

18. The pharmaceutical composition of claim 13, wherein the single-chain insulin is formulated at a concentration of 0.6 mM to 5.0 mM.

19. The pharmaceutical composition of claim 13, wherein the single-chain insulin is formulated at a strength of U-100, U-200, U-300, U-400, or U-500.

20. A method for lowering the blood sugar level of a patient in need thereof, the method comprising, subcutaneously administering a pharmaceutical composition to the patient, wherein the pharmaceutical composition comprises a single-chain insulin formulated at a pH within the range 7.0 to 8.0, and wherein the single chain insulin comprises:
- a C-domain of from 6 to 11 amino acid residues comprising at least two acidic residues at the N-terminal side of the C-domain and at least two basic residues at the C-terminal side of the C-domain peptide, wherein the amino acids at the N-terminal side of the C-domain are the amino acids Glu-Glu;
- a basic amino acid residue at the position corresponding to A8 of human insulin, and
- an acidic amino acid residue at the position corresponding to A14 of human insulin.

* * * * *